United States Patent
Burd

(10) Patent No.: US 11,255,838 B2
(45) Date of Patent: *Feb. 22, 2022

(54) LEVELS, FUNCTIONS, AND RESISTANCES RELATED TO CHRONIC CONDITIONS BY USING LYSINE-BASED SUPPLEMENTS

(71) Applicant: Lysulin, Inc., San Diego, CA (US)

(72) Inventor: John Burd, San Diego, CA (US)

(73) Assignee: LYSULIN, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/865,064

(22) Filed: May 1, 2020

(65) Prior Publication Data

US 2020/0256846 A1 Aug. 13, 2020

Related U.S. Application Data

(63) Continuation-in-part of application No. 15/817,574, filed on Nov. 20, 2017, now Pat. No. 10,653,720.

(60) Provisional application No. 62/581,573, filed on Nov. 3, 2017.

(51) Int. Cl.

| | |
|---|---|
| *G01N 33/49* | (2006.01) |
| *A23L 33/15* | (2016.01) |
| *A61K 31/198* | (2006.01) |
| *A61K 33/30* | (2006.01) |
| *A61K 31/375* | (2006.01) |
| *G01N 33/493* | (2006.01) |
| *A23L 33/16* | (2016.01) |
| *A23L 33/175* | (2016.01) |
| *G01N 33/68* | (2006.01) |
| *G01N 33/70* | (2006.01) |
| *G01N 33/66* | (2006.01) |
| *G01N 33/92* | (2006.01) |
| *G01N 33/72* | (2006.01) |

(52) U.S. Cl.
CPC .......... *G01N 33/492* (2013.01); *A23L 33/15* (2016.08); *A23L 33/16* (2016.08); *A23L 33/175* (2016.08); *A61K 31/198* (2013.01); *A61K 31/375* (2013.01); *A61K 33/30* (2013.01); *G01N 33/493* (2013.01); *G01N 33/66* (2013.01); *G01N 33/6812* (2013.01); *G01N 33/6827* (2013.01); *G01N 33/70* (2013.01); *G01N 33/721* (2013.01); *G01N 33/92* (2013.01); *G01N 2800/52* (2013.01)

(58) Field of Classification Search
CPC .... G01N 33/492; G01N 33/493; G01N 33/66; G01N 33/6812; G01N 33/6827; G01N 33/70; G01N 33/721; G01N 33/92; G01N 2800/52; A23L 33/175; A23L 33/16; A23L 33/15; A61K 31/375; A61K 31/198; A61K 33/30

See application file for complete search history.

(56) References Cited

U.S. PATENT DOCUMENTS

| | | |
|---|---|---|
| 8,060,249 B2 | 11/2011 | Bear et al. |
| 2003/0082074 A1 | 5/2003 | Jurik et al. |
| 2004/0060859 A1 | 4/2004 | Seshimoto |
| 2007/0238770 A1 | 10/2007 | Gougoutas |
| 2008/0004507 A1 | 1/2008 | Williams |
| 2008/0014644 A1 | 1/2008 | Barasch |
| 2008/0027024 A1 | 1/2008 | Gahler et al. |
| 2013/0035563 A1 | 2/2013 | Angelides |
| 2014/0044828 A1 | 2/2014 | Mine et al. |
| 2014/0227371 A1 | 8/2014 | Heath |
| 2014/0256806 A1 | 9/2014 | Takaka |
| 2014/0363896 A1 | 12/2014 | Suzuki |
| 2015/0038453 A1 | 2/2015 | Hageman |
| 2015/0160218 A1 | 6/2015 | Demirci |
| 2015/0182483 A1 | 7/2015 | Goldberg |
| 2016/0263317 A1 | 9/2016 | Arefieg |
| 2017/0061823 A1 | 3/2017 | Cohen |
| 2017/0255758 A1 | 9/2017 | Washko |

FOREIGN PATENT DOCUMENTS

| | | |
|---|---|---|
| CN | 10164268 A1 | 2/2010 |
| CN | 102772215 | 11/2012 |
| CN | 104138469 | 1/2014 |
| WO | WO2004035074 A1 | 4/2004 |
| WO | WO2005123108 A1 | 12/2005 |
| WO | WO2008120797 A1 | 9/2008 |
| WO | WO2010017190 A1 | 2/2010 |
| WO | WO2011086507 A1 | 7/2011 |

OTHER PUBLICATIONS

Maurer, Dr. Richard, "HOMA-IR: What it is & why you should know yours," The Blood Code, Sep. 20, 2016, <https://www.thebloodcode.com/homa-ir-know/.
Nah et al., "Annals of Laboratory Medicine, Comparison of Urine Albumin-to-Creatinine Ratio (ACR) between ACR strip test and quantitative test in Prediabetes and Diabetes," Jan. 2017.
Clinitek Advantus Analyzer, Siemens, Operator's Guide, Jun. 2006.
Sulochana et al., "Effect or oral supplementation of free amino acids in type 2 diabetic patients—a pilot clinical trial," Medical Science Monitor, 2002, 8(3), CR131-137.
Healthy Care Australia, Product Label for Super Lysine Cold Sore Relief, <http://healthycare.com.au/index.php/our-products/all-products/item/hc-super-lysine-cold-sore-relief-100-tablets>.

(Continued)

*Primary Examiner* — Genevieve S Alley
(74) *Attorney, Agent, or Firm* — Sheppard, Mullin, Richter & Hampton LLP

(57) ABSTRACT

Systems and method that relate to improving levels, functions, and resistances related to chronic conditions by using lysine-based supplements are described. For example, a method of monitoring an analyte level may include administering a supplement that may include lysine, zinc, and vitamin C to a user. The method may also include monitoring an analyte level in a bio-sample before and after the supplement is administered.

18 Claims, 18 Drawing Sheets

(56) References Cited

OTHER PUBLICATIONS

Chen, English machine translation of CN101642468.
Hirabayashi, English machine translation of WO 2008/120797.
Zhu, English machine translation of CN 102772215.
Jayawardena et al., "Effects of zinc supplementation on diabetes mellitus: a systematic review and meta-analysis." Diabetology & Metabolic Syndrome, 2012, pp. 1-15, <http://www.nbci.nlm.nih.gov/pmc/articles/PMC3407731/>.
Khayat, Y., "Anti-Glycation Supplements Part III (Glycation: Part II of II)," Perspectives on Health, Jan. 26, 2015 Jan. 26, 2015), pp. 1-52. Retrieved from the internet: <https://yochanakhayat.wordpress.com/2015/01/26/anti- glycation-supplements-part-iii-glycation-part-ii-of-ii/> on Mar. 6, 2018 (Mar. 6, 2018). entire document.
International Search Report and Written Opinion corresponding to International PCT Application No. PCT/US2018/015587 dated Apr. 13, 2018.
NHS, Point-of-care Creatinine Testing for the Detection and Monitoring of Chronic Kidney Disease, Horizon Scan Report 0038, Mar. 2014.
Examiner.com, "Zinc", published online: Nov. 1, 2016; obtained via Internet Archive Wayback Machine on Apr. 26, 2018.
Hirabayashi el al., WO 2008/120797, Published Oct. 9, 2008, English machine translation obtained on Apr. 26, 2018.
National Institute for Health Research, "Point-of-Care Creatinine Testing for the Detection and Monitoring of Chronic Kidney Disease," NIHR Diagnostic Evidence Cooperative Oxford; Mar. 2014, p. 2 heading details of technology; p. 3, heading importance and table 1; p. 5, second paragraph.
NOVA Biomedical, "StatSensor Point-of-Care Whole Blood Creatinine and eGRF Testing," May 2008; (retrieved Mar. 8, 2018]. Retrieved from the Internet; <URL: http://novamed.dk/Llf/30000_39999/38239/2027ea11fdbd525ddc1c17d1ab983a44.pdf>; p. 2, photograph; p. 8, heading docking station.
International Search Report and Written Opinion corresponding to International PCT Application PCT/US2018/015589 dated Mar. 22, 2018.
Medtronic "Guardian Real-Time Continuous Glucose Monitoring System" 2006; (retrieved Mar. 6, 2018).
International Search Report and Written Opinion corresponding to International PCT Application PCT/US2018/015593 dated Mar. 26, 2018.
Examination Report in IN Patent Application No. 202017019560, dated Apr. 8, 2021.

| CKD stage | GFR level (mL/min/1.73 m²) |
|---|---|
| Stage 1 | ≥ 90 |
| Stage 2 | 60 – 89 |
| Stage 3 | 30 – 59 |
| Stage 4 | 15 – 29 |
| Stage 5 | < 15 |

FIG. 8

| Albuminuria categories in CKD | | |
|---|---|---|
| Category | ACR (mg/g) | Terms |
| A1 | <30 | Normal to mildly increased |
| A2 | 30-300 | Moderately increased* |
| A3 | > 300 | Severely increased** |

*Relative to young adult level. ACR 30-300 mg/g for > 3 months indicated CKD.
**Including nephrotic syndrom (albumin excretion ACR > 2220 mg/g)

*FIG. 9*

| Categories | Triglyceride level (mg/dL) |
|---|---|
| Normal | ≤ 150 |
| Borderline High | 150–199 |
| High | 200–499 |
| Very High | ≥500 |

*FIG. 10*

Table 2: Baseline characteristics of the Lysulin™ and Placebo groups

| | Mean (±SD) | | |
|---|---|---|---|
| | Lysulin™ Group (n=55) | Placebo Group (n=100) | p value |
| Age (years) | 46.2 (±9.6) | 44.5 (±10.6) | NS |
| Blood Pressure | | | |
| Systolic blood pressure (mmHg) | 129.3 (±17.5) | 136.0 (±19.0) | NS |
| Diastolic blood pressure (mmHg) | 77.3 (±10.6) | 81.5 (±9.4) | NS |
| Anthropometric parameters | | | |
| Body mass index (kg/m$^2$) | 26.1 (±3.4) | 24.6 (±3.7) | NS |
| Waist circumference (cm) | 86.9 (±8.6) | 87.5 (±7.9) | NS |
| Hip circumference (cm) | 94.1 (±6.7) | 95.5 (±6.4) | NS |
| Waist to Hip ratio | 0.92 (±0.06) | 0.92 (±0.07) | NS |
| Physical Activity | 830 (±1123) | 782 (±1318) | NS |
| Dietary Intake | | | |
| Total energy (kcal/day) | 1658.1 (±459.5) | 1771.1 (±420.3) | NS |
| Carbohydrate (g/day) | 353.1 (±98.5) | 392.4 (±96.9) | NS |
| Protein (g/day) | 42.2 (±17.4) | 45.2 (±16.1) | NS |
| Fat (g/day) | 46.9 (±14.2) | 55.9 (±18.1) | 0.004 |
| Dietary fiber (g/day) | 15.6 (±7.9) | 16.9 (±8.4) | NS |
| Biochemical parameters | | | |
| Fasting Plasma Glucose (mg/dl) | 108.9 (±13.7) | 107.3 (±13.3) | NS |
| 2hr OGTT Plasma Glucose (mg/dl) | 142.0 (±15.7) | 149.2 (±15.5) | NS |
| HbA1C (%) | 5.9 (±0.5) | 6.1 (±0.7) | NS |
| Serum insulin (μIU/l) | 11.8 (±6.0) | 13.1 (±9.9) | NS |
| Insulin resistance | 1.3 (±0.5) | 1.1 (±0.5) | NS |
| β-cell function (%) | 52.9 (±19.2) | 51.1 (±22.7) | NS |
| Total cholesterol (mg/dl) | 199.1 (±32.5) | 176.0 (±31.9) | <0.001 |
| LDL cholesterol (mg/dl) | 129.6 (±38.9) | 135.3 (±32.8) | NS |
| HDL cholesterol (mg/dl) | 46.1 (±11.5) | 55.4 (±19.9) | NS |
| Triglycerides (mg/dl) | 130.5 (±54.4) | 126.2 (±51.0) | NS |
| Alanine aminotransferase (U/l) | 23.4 (±10.0) | 24.1 (±11.7) | NS |
| Aspartate aminotransferase (U/l) | 29.4 (±7.9) | 27.9 (±11.8) | NS |
| Serum bilirubin (mg/dl) | 0.6 (±0.4) | 0.6 (±0.3) | NS |
| Serum creatinine (mg/dl) | 0.8 (±0.2) | 0.7 (±0.2) | NS |

HDL – High Density Lipoprotein; LDL – Low Density Lipoprotein; NS – Not Significant; OGTT – Oral Glucose Tolerance Test; SD – Standard Deviation

FIG. 15

|  | Mean±SD | | | |
|---|---|---|---|---|
|  | Visit 0 (Baseline) (n=110) | Visit 1 (1 month) (n=105) | Visit 2 (3 months) (n=94) | Visit 3 (6 months) (n=83) |
| FPG (mg/dl) | | | | |
| Lysulin™ | 108.9 (±13.7)[#‡] | 109.9 (±11.5) | 97.2 (±9.8)[#] | 95.2 (±8.7)[‡] |
| Placebo | 107.3 (±13.3) | 111.1 (±10.4) | 105.2 (±9.3) | 109.9 (±16.0) |
| 2hr OGTT PG (mg/dl) | | | | |
| Lysulin™ | 142.0 (±15.7)[#‡] | 142.3 (±10.5) | 134.9 (±18.8)[#] | 136.0 (±11.2)[‡] |
| Placebo | 149.2 (±15.5)[#] | 151.6 (±19.9) | 162.8 (±12.5)[#] | 155.2 (±16.9) |
| HbA1c (%) | | | | |
| Lysulin™ | 5.9 (±0.5)[#‡] | NM | 5.5 (±0.5)[#] | 5.4 (±0.3)[‡] |
| Placebo | 6.1 (±0.7)[#] | NM | 6.4 (±0.6)[#] | 6.3 (±0.6) |
| Insulin resistance | | | | |
| Lysulin™ | 1.3 (±0.5)[#] | NM | NM | • (±0.4)[#] |
| Placebo | 1.1 (±0.5) | NM | NM | 1.3 (±0.7) |
| β-cell function (%) | | | | |
| Lysulin™ | 52.9 (±19.2)[#] | NM | NM | 71.9 (±10.5)[#] |
| Placebo | 51.1 (±22.7) | NM | NM | 49.6 (±15.0) |

*FIG. 16*

|  | Mean±SD | | | |
| --- | --- | --- | --- | --- |
|  | Visit 0 (Baseline) (n=110) | Visit 1 (1 month) (n=105) | Visit 2 (3 months) (n=94) | Visit 3 (6 months) (n=83) |
| Systolic BP(mmHg) | | | | |
| Lysulin™ | 129.3 (±17.5) | 132.1 (±15.1) | 127.3 (±17.2) | 135.3 (±19.5) |
| Placebo | 136.0 (±19.0) | 129.9 (±17.1) | 135.2 (±19.9) | 134.5 (±18.9) |
| Diastolic BP(mmHg) | | | | |
| Lysulin™ | 77.3 (±10.6) | 75.1 (±9.9) | 81.9 (±13.9) | 80.1 (±8.1) |
| Placebo | 81.5 (±9.4) | 79.9 (±10.4) | 85.0 (±10.1) | 79.5 (±9.9) |
| Body mass index(kg/m$^2$) | | | | |
| Lysulin™ | 26.1 (±3.4) | 25.9 (±4.1) | 24.8 (±5.1) | 25.1 (±3.8) |
| Placebo | 24.6 (±3.7) | 25.4 (±4.9) | 25.2 (±4.9) | 24.5 (±4.6) |
| Waist circumference(cm) | | | | |
| Lysulin™ | 86.9 (±8.6) | 87.6 (±9.1) | 86.3 (±8.7) | 88.2 (±9.1) |
| Placebo | 87.5 (±7.9) | 86.4 (±8.1) | 86.1 (±9.5) | 87.0 (±8.9) |
| Hip circumference(cm) | | | | |
| Lysulin™ | 94.1 (±6.7) | 95.0 (±7.2) | 96.1 (±9.5) | 93.8 (±8.5) |
| Placebo | 95.5 (±6.4) | 93.1 (±9.9) | 95.7 (±9.6) | 96.7 (±6.9) |
| Waist to Hip ratio | | | | |
| Lysulin™ | 0.92 (±0.06) | 0.92 (±0.05) | 0.90 (±0.06) | 0.94 (±0.05) |
| Placebo | 0.92 (±0.07) | 0.93 (±0.07) | 0.89 (±0.08) | 0.90 (±0.06) |

FIG. 17

| | Visit 0 (Baseline) (n=110) | Visit 1 (1 month) (n=105) | Visit 2 (3 months) (n=94) | Visit 3 (6 months) (n=83) |
|---|---|---|---|---|
| Total cholesterol(mg/dl) | | | | |
| Lysulin™ | 199.1 (±32.5)#‡ | NM | 184.0 (±33.2)# | 172.1 (±29.1)‡ |
| Placebo | 176.0 (±31.9) | NM | 182.9 (±30.1) | 186.9 (±23.9) |
| LDL cholesterol(mg/dl) | | | | |
| Lysulin™ | 129.6 (±38.9)#‡ | NM | 105.9 (±20.1)# | 117.5 (±16.9)‡ |
| Placebo | 135.3 (±32.8) | NM | 130.2 (±23.8) | 128.9 (±38.1) |
| HDL cholesterol(mg/dl) | | | | |
| Lysulin™ | 46.1 (±11.5) | NM | 45.2 (±9.1) | 44.9 (±8.9) |
| Placebo | 53.4 (±19.9) | NM | 56.1 (±15.2) | 50.1 (±19.1) |
| Triglycerides(mg/dl) | | | | |
| Lysulin™ | 130.5 (±54.4) | NM | 129.5 (±28.2) | 118.2 (±39.9) |
| Placebo | 126.2 (±51.0)#‡ | NM | 107.1 (±33.9)# | 108.5 (±21.9)‡ |

Mean±SD

*FIG. 18*

LEVELS, FUNCTIONS, AND RESISTANCES RELATED TO CHRONIC CONDITIONS BY USING LYSINE-BASED SUPPLEMENTS

RELATED APPLICATIONS

This application is a continuation-in-part of and claims the benefit of U.S. patent application Ser. No. 15/817,574, filed on Nov. 20, 2017, which claims benefit of U.S. Provisional Patent Application No. 62/581,573, filed on Nov. 3, 2017, the contents of which are incorporated herein by reference in their entirety.

FIELD

The present disclosure is generally related to improving chronic conditions and more specifically, embodiments of the present disclosure relate to improving levels, functions, and resistances related to chronic conditions by using lysine-based supplements.

BRIEF SUMMARY OF EMBODIMENTS

Disclosed are systems and method that relate to improving levels, functions, and resistances related to chronic conditions by using lysine-based supplements. For example, a method of monitoring an analyte level may include administering a supplement that may include lysine, zinc, and vitamin C to a user. The method may also include monitoring an analyte level in a bio-sample before and after the supplement is administered.

In embodiments, a lysine portion of the supplement may include D-lysine.

In embodiments, a lysine portion of the supplement may include L-lysine.

In embodiments, monitoring the analyte level may include analyzing blood samples.

In embodiments, monitoring the analyte level may include analyzing urine samples.

In embodiments, the analyte may include one of lysine, triglyceride, cholesterol, blood glucose, HbA1c, albumin, and creatinine.

In embodiments, the analyte level may include one of a lysine level, triglyceride level, cholesterol level, beta-cell function, insulin resistance, blood glucose level, HbA1c level, albumin level, and creatinine level.

In embodiments, the supplement may include a range of about 500 mg to about 3000 mg of lysine.

In embodiments, the supplement may include a range of less than about 200 mg of zinc.

In embodiments, the supplement may include a range of about less than about 500 mg of vitamin C.

In embodiments, the supplement may include a range of about 500 mg to about 2000 mg of lysine, less than about 200 mg of zinc, and less than about 500 mg of vitamin C.

In one example, a method of improving an analyte level in a user may include administering a supplement that may include lysine, zinc, and vitamin C to the user. The method may also include monitoring an analyte level in a bio-sample before and after the supplement is administered. The method may include determining a change in a dose of the supplement based on the analyte level found in the bio-sample after the supplement is administered.

In embodiments, the method may further include providing a notification on an automatic reader regarding a precise dosage of supplement to be administered.

In embodiments, the notification may include a pop-up, a vibration, or a noise.

In embodiments, determining a change in dose may include using a visual test to determine an amount of supplement to be administered. The visual test may include exposing the bio-sample to a reagent that causes a visible indication of the analyte level within the bio-sample.

In embodiments, the analyte level may include one of a lysine level, triglyceride level, cholesterol level, beta-cell function, insulin resistance, blood glucose level, HbA1c level, albumin level, and creatinine level.

In embodiments, the supplement may include a range of about 500 mg to about 2000 mg of lysine, less than about 200 mg of zinc, and less than about 500 mg of vitamin C.

In another example, a method of improving an insulin resistance for a user with pre-diabetes may include administering a supplement that may include lysine, zinc, and vitamin C to the user with pre-diabetes.

In one example, a method of improving a beta-cell function for a user with pre-diabetes may include administering a supplement that may include lysine, zinc, and vitamin C to the user with pre-diabetes.

In another example, a method of reducing the progression to diabetes for a user with pre-diabetes may include administering a supplement that may include lysine, zinc, and vitamin C to the user with pre-diabetes.

BRIEF DESCRIPTION OF THE DRAWINGS

The present disclosure, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention.

FIG. 8 is a table illustrating the relationship between a stage of chronic kidney disease and the related glomerular filtration rate range, consistent with embodiments disclosed herein.

FIG. 9 is a table illustrating the relationship between a stage of chronic kidney disease and the related albumin-to-creatinine ratio, consistent with embodiments disclosed herein.

FIG. 10 is a table illustrating the relationship between a category of triglyceride levels and the related triglyceride levels, consistent with embodiments disclosed herein.

FIG. 15 illustrates the effect of a supplement on a sample group compared to a group on placebos, in accordance with various embodiments of the present disclosure.

FIG. 16 illustrates the effect of a supplement on a sample group compared to a group on placebos, in accordance with various embodiments of the present disclosure.

FIG. 17 illustrates the effect of a supplement on a sample group compared to a group on placebos, in accordance with various embodiments of the present disclosure.

FIG. 18 illustrates the effect of a supplement on a sample group compared to a group on placebos, in accordance with various embodiments of the present disclosure.

Figure 1:
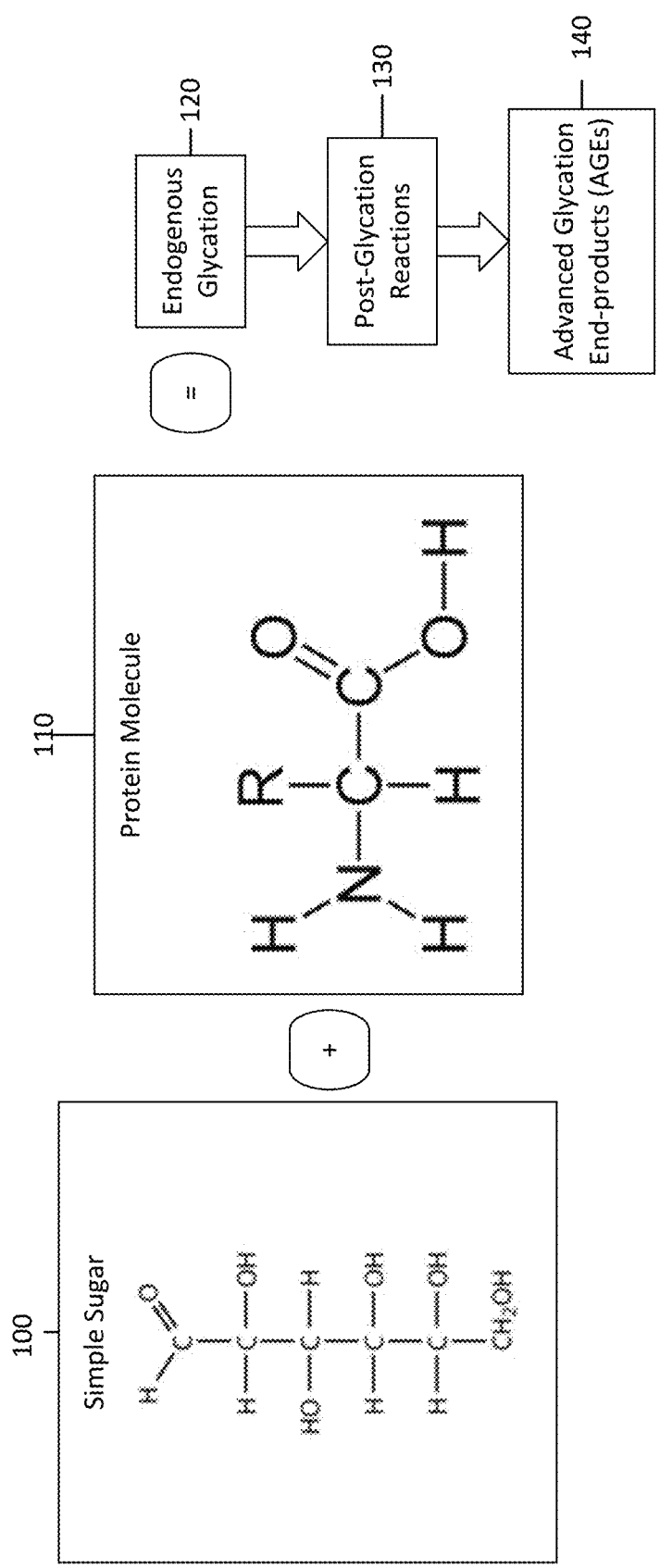
FIG. 1 is a diagram illustrating an example of endogenous glycation, consistent with embodiments disclosed herein.

These figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

The present disclosure is directed towards treatment of liver disease, pancreas disease, blood disorders, diabetes, pre-diabetes, and/or kidney disease using supplements including lysine, zinc, and/or vitamin C. More specifically, embodiments disclosed herein are directed towards methods for improving levels, functions, and resistances related to chronic conditions by using lysine-based supplements. For example, this may include improving a lysine level, triglyceride level, cholesterol level, beta-cell function, insulin resistance, blood glucose level, HbA1c level, albumin level, creatinine level, and/or another level, as well as chronic hepatological, pancreatic, blood, and nephrological disorders, using supplements including lysine, zinc, and/or vitamin C. The supplements may compete with existing protein and lipid molecules settled within the body to reduce the number of glycated proteins and to prevent AGEs. Embodiments disclosed herein may also be directed toward methods for detecting a lysine level, triglyceride level, cholesterol level, beta-cell function, insulin resistance, blood glucose level, HbA1c level, albumin level, creatinine level, and albumin-creatinine ratio (ACR) level, which may indicate CKD, using a portable mid-infrared (mid-IR) device. Supplements including lysine, zinc, and/or vitamin C may be used to treat liver disease (e.g., non-alcoholic fatty liver disease (NAFLD), hepatic steatosis, etc.), pancreatitis, CKD, and/or blood disorders. For example, combined supplement formulations of lysine, zinc, and/or vitamin C may interact with simple sugars that might otherwise interact with existing proteins to create glycated proteins and AGEs that lead to various chronic health problems. In one example, the supplement may include a range of about 500 mg to about 3000 mg of lysine, a range of about 5 mg to about 200 mg of zinc, and a range of about 50 mg to about 500 mg of vitamin C. In other embodiment, the ranges of lysine, zinc, or vitamin C may be different. The effectiveness of the supplements may be measured through a bio-sample analysis, such as a blood test, for hemoglobin A1c, lysine, triglyceride, cholesterol, blood glucose, HbA1c, albumin, creatinine, and/or another analyte. In some embodiments, the effectiveness of the supplements may be measured using a mid-infrared (mid-IR) device comparing an albumin-creatinine ratio in urine. The inclusion of zinc significantly increases the efficacy of a supplement including only lysine. The inclusion of zinc allows for the reduction in dosage/pill size with same or better results. The inclusion of vitamin C may further reduce the effects of pre-diabetes, diabetes, CKD, pancreatic disease, and liver disease, as well as improve a lysine level, triglyceride level, cholesterol level, beta-cell function, insulin resistance, blood glucose level, HbA1c level, albumin level, creatinine level, and/or other level. In some embodiments, a meter may be used to measure a lysine level, triglyceride level, cholesterol level, beta-cell function, insulin resistance, blood glucose level, HbA1c level, albumin level, creatinine level, a glomerular filtration rate (GFR), and a stage of CKD based on the other measurements. This meter may be independent of any supplement ingestion.

Glycation is the bonding of a simple sugar to a protein or lipid molecule. Glycation may be either exogenous (i.e., outside the body) or endogenous (i.e., inside the body). Endogenous glycation mainly occurs in the bloodstream to absorbed simple sugars, such as glucose, fructose, and galactose. Glycation is the first change of these molecules in a slow multi-step process which leads to advanced glycation end products (AGEs). Because AGEs are irreversible end products of a glycation process, stopping the glycation process before AGEs form is important. AGEs may be benign, but many are implicated in many age-related chronic diseases such as liver disease, pancreas disease, pre-diabetes, diabetes, cardiovascular diseases, Alzheimer's disease, cancer, chronic kidney disease (CKD), atherosclerosis, peripheral neuropathy, and other sensory losses such as deafness. Preventing this process may also help regulate creatinine levels of people with diabetes and creatinine levels and/or albumin levels of people with CKD. It may also help regulate and/or lower triglyceride levels. The dietary supplement may also help improve cholesterol (e.g., total and LDL cholesterol), blood glucose, HbA1c, lysine, beta-cell function, blood glucose, and insulin resistance levels. It may also help reduce the progression to diabetes for people with pre-diabetes and may improve beta-cell function for those with pre-diabetes.

FIG. 1 is a diagram illustrating an example of endogenous glycation. As illustrated in FIG. 1, the absorbed simple sugars 100 may include glucose. As is known in the art, the simple sugars may also include fructose and galactose. Fructose experiences up to ten times the amount of glycation activity compared to glucose. As an example, FIG. 1 illustrates the structural formula for glucose. Simple sugar 100 may interact with a protein molecule 110 resulting in endogenous glycation 120. As an example, the general structural formula for an amino acid is also illustrated in FIG. 1. Various other proteins may interact with the simple sugar 100. In another embodiment, various lipid molecules may interact with the simple sugar 100. In particular, with endogenous glycation, the covalent bonding between simple sugar 100 and protein molecule 110 may occur without the control of an enzyme. Endogenous glycation occurs mainly in the bloodstream.

Glycation 130 may be a first step before these new molecules undergo post glycation reactions 140, such as Schiff base and Amadori reactions. For example, the aldehyde group of a glucose molecule may combine with the amino group of a L-lysine molecule, from a protein molecule, to form a Schiff base. In essence, a double bond may be formed between the glucose's carbon atoms and the lysine's nitrogen atoms. The Amadori product rearranges the formation of the Schiff base. As a result, AGEs 150 may be formed. For example, when an Amadori product may be oxidized, AGEs 150 are formed. While some AGEs are benign, others may contribute to pre-diabetes, diabetes, liver disease, pancreatitis, cardiovascular disease, chronic kidney disease, cancer, and other chronic diseases.

Figure 2:
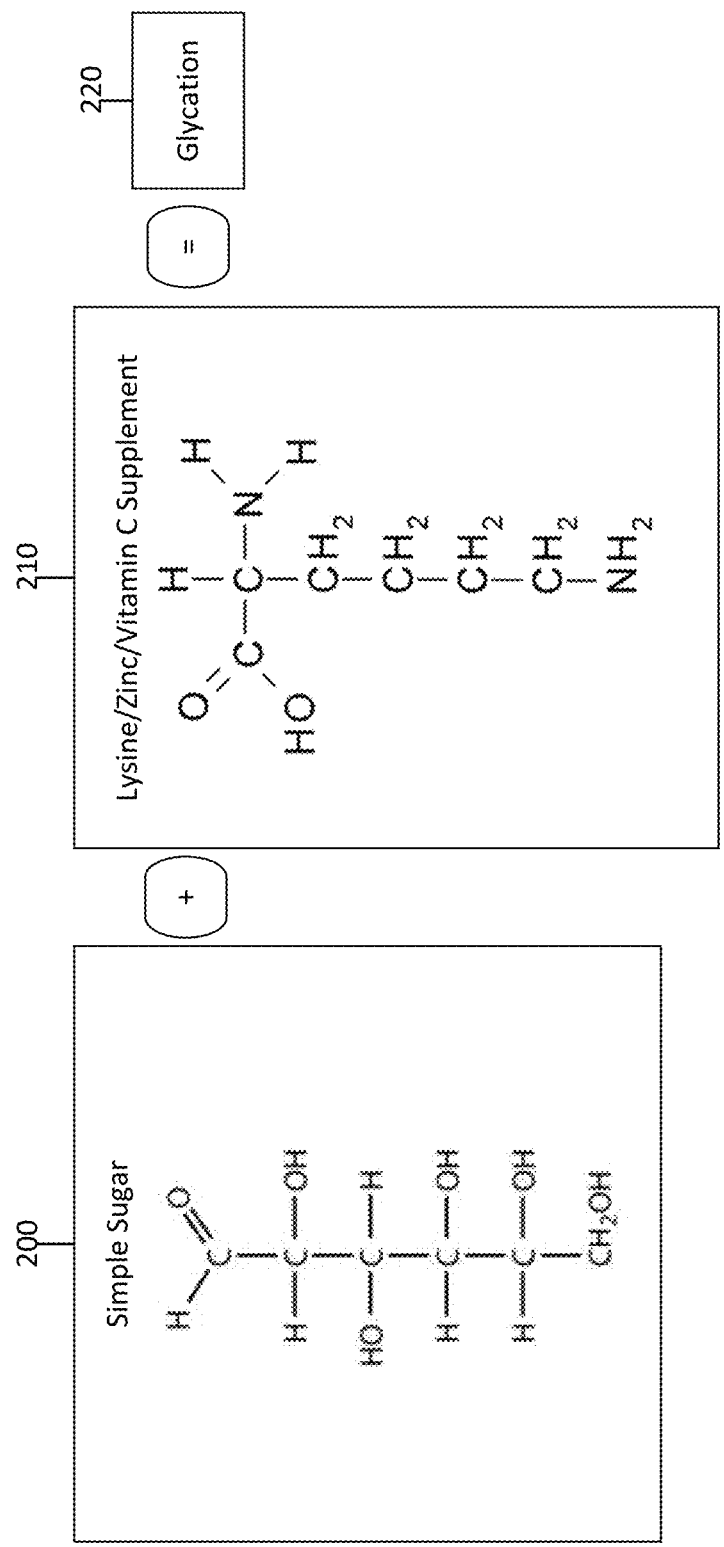
FIG. 2 is a diagram illustrating an example of glycation occurring with a supplement including lysine, zinc, and/or vitamin C, consistent with embodiments disclosed herein.

FIG. 2 is a diagram illustrating an example of glycation occurring with a supplement including lysine, zinc, and/or vitamin C. In this case, the simple sugars 200 interact with the supplement including lysine, zinc, and/or vitamin C 210 instead of the protein molecule 110. As described above, Schiff bases form when the amino group of a lysine molecule, which is a part of a protein molecule, covalently bond with the aldehyde group of a glucose molecule. However, when a supplement including lysine, zinc, and/or vitamin C is administered, the aldehyde group of a glucose molecule may bind to the lysine instead of the lysine molecule portion of the protein molecule. The supplement may use D-lysine or L-lysine. Glycation 220 may occur, but AGEs are prevented from occurring within the body, and glycated hemoglobin may be reduced. Even if Amadori products occur and AGEs form, they are not introduced into the body because the glycated lysine may be harmlessly removed through the urine. As set forth herein, it has been determined that the inclusion of zinc significantly increases the efficacy of a supplement including lysine, thereby allowing for a significant reduction in dosage/pill size with same or better results. In some embodiments, a dietary supplement may include a combination of lysine, zinc, vitamin C and other nutritional supplements, e.g., vitamin B12, vitamin E, or other nutritional supplements. For example, a dietary supplement including lysine, zinc, and/or vitamin C may improve immune system functionality, lower glucose levels, and reduce triglycerides. The dietary supplement may also help improve lysine levels, triglyceride levels, cholesterol levels, beta-cell function, insulin resistance, blood glucose levels, HbA1c levels, albumin levels, and/or creatinine levels. It may also help reduce the progression to diabetes for people with pre-diabetes and may improve beta-cell function.

Figure 3:
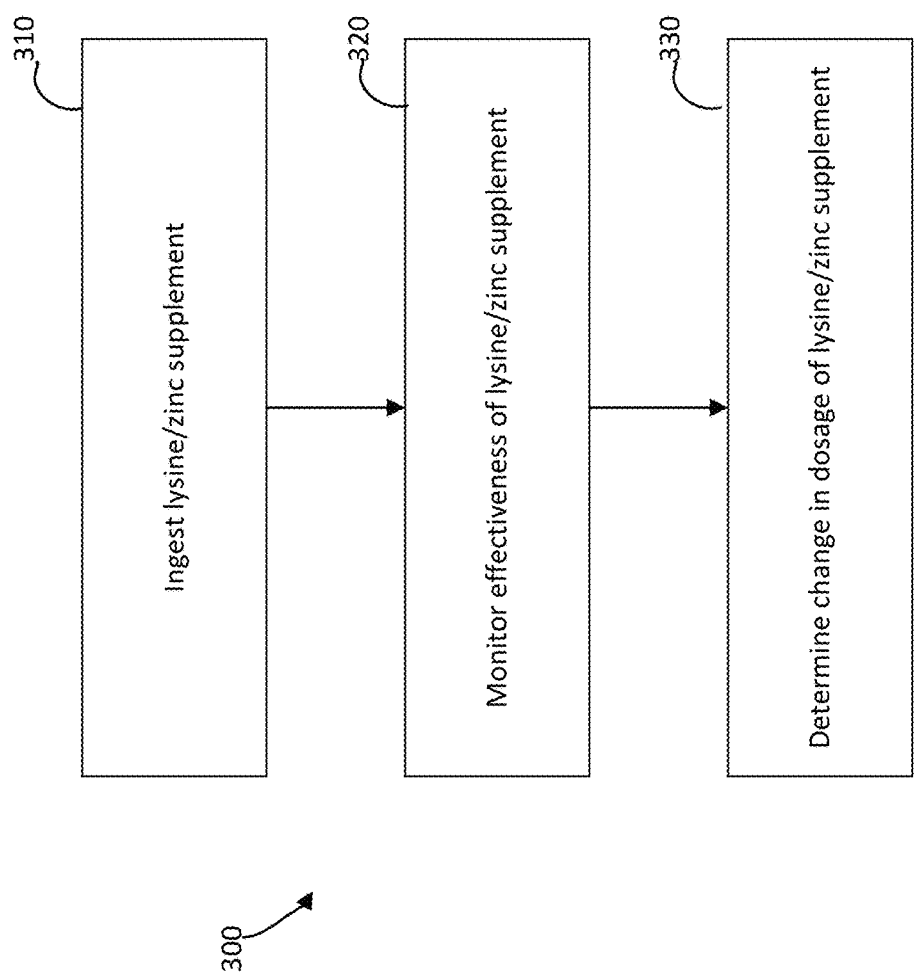
FIG. 3 is a flow chart illustrating an example method of monitoring the effectiveness of supplements from a bio-sample, consistent with embodiments disclosed herein.

FIG. 3 is a flow chart illustrating an example method of monitoring the effectiveness of supplements including lysine, zinc, and/or vitamin C from a bio-sample 300. For example, method 300 may include administering the supplement at step 310. For example, the supplement may include a range of about 500 mg to about 3000 mg of lysine, a range of about 5 mg to about 200 mg of zinc, and a range of about 50 mg to about 500 mg of vitamin C. In other embodiments, the ranges of lysine, zinc, or vitamin C may be different. In still other embodiments, the supplement may include lysine and zinc, lysine and/or vitamin C, lysine, zinc, and/or vitamin C, and/or other combinations. The supplement may be administered in a pill, gummy, tablet, shake, capsule, liquid extract, drink, or nutritional bar medium. The supplement may also come in various other mediums. The lysine portion of the supplement may be D-lysine or L-lysine. D-lysine, is not naturally produced within the body, and has similar chemical characteristics to L-lysine. Simple sugars may interact with D- and L-lysine in lieu of free amino groups in structural proteins within the system. L-lysine occurs naturally in the body. Naturally occurring L-lysine may be a side-chain residue of ingested protein. L-lysine may have a bitter and/or sweet taste, making it more suitable for particular supplement mediums.

Method 300 may also include monitoring the effectiveness of the supplement at step 320. In some embodiments, effectiveness of the lysine treatment may be monitored by analyzing blood and/or urine samples. The glycated lysine may harmlessly pass through the urine upon interacting with simple sugars. A urine sample may be obtained and analyzed using a fructosamine test that measures glycated lysine. In other embodiments, a urine sample and/or a blood sample can be analyzed using a visual test. For example, some urine tests may expose the urine sample to a reagent which causes a color change indicating the concentration range of lysine within the urine or a triglyceride level in blood. The sample may also test a lysine level, triglyceride level, cholesterol level, beta-cell function, insulin resistance, blood glucose level, HbA1c level, albumin level, creatinine level, and/or another level. A first color may indicate a healthy level of lysine, triglyceride, cholesterol, beta-cell function, insulin resistance, blood glucose, HbA1c, albumin, and/or creatinine in the sample, as discussed herein. A healthy level of lysine may depend on the amount of lysine that is glycated, the number of supplements taken, and a given user. A healthy level of triglycerides may be less than about 150 mg/dL, but it should be appreciated that what is healthy for a particular user may vary. A second color may indicate an unhealthy level of lysine, triglyceride, cholesterol, beta-cell function, insulin resistance, blood glucose, HbA1c, albumin, and/or creatinine in the sample, as discussed herein. An unhealthy amount of lysine may be low, indicating not much lysine was glycated. An unhealthy amount of lysine may be above 500 mg/dL, but it should be appreciated that the values may vary based on a user. It should be appreciated that more than two colors may be used to increase the granularity of the test.

In some embodiments, a more precise test may be used to indicate quantitative levels of glycated lysine in the urine sample. In addition, the urine sample may also be used to monitor creatinine and/or albumin control, particularly useful for people with chronic kidney disease. As the supplement interacts with sugar, less hemoglobin may be glycated as a result. As a result, blood glucose levels, HbA1c levels, and/or triglyceride levels may decrease. Moreover, the supplement may reduce creatinine levels and/or albumin levels. The sample may also be used to monitor a lysine level, triglyceride level, cholesterol level, beta-cell function, insulin resistance, blood glucose level, HbA1c level, albumin level, creatinine level, and/or another level.

Creatinine is a compound that is produced by metabolism of creatine. Creatinine travels through the bloodstream to the kidneys. Kidneys filter out some portion of creatinine, and the remaining creatinine may be excreted through the urine. Creatinine levels may be an indicator of kidney function. Increased creatinine levels may indicate impaired kidney function, since the kidney is not able to filter out as much creatinine. Creatinine may be measured through blood tests or urine tests. Creatinine levels may be used in determining a glomerular filtration rate (GFR), a more precise measurement of kidney function than creatinine levels alone, described herein.

GFR describes the flow rate of filtered fluid through the kidney. Using creatinine levels, age, gender, race, and/or other factors, the GFR may be determined. The GFR value may be used to determine a stage of CKD, as shown in FIG. 8.

Albumin may be a simple form of a protein made by the liver. Albumin may be an indicator of kidney function. Increased albumin levels may indicate impaired kidney function. Albumin may be measured through blood tests or urine tests. Albumin levels and creatinine levels may be used in determining an albumin-to-creatinine ratio (ACR), a more precise measurement of kidney function than albumin levels or creatinine levels alone. ACR may be measured by dividing albumin concentration, in milligrams, by creatinine concentration, in grams.

Triglyceride may refer to a type of lipid found in blood. Triglycerides may be an indicator of heart health, as high triglycerides may contribute to the risk of stroke, heart attack, and heart disease more generally. High triglyceride levels may also be a sign of type 2 diabetes, low levels of thyroid, metabolic syndrome, or other conditions. Triglyceride levels may be tested through blood tests, such as a lipid panel. Normal triglyceride levels may be less than about 150 mg/dL (milligrams per deciliter) (about 1.7 mmol/L (millimoles per liter)). Near high triglyceride levels may be about 150 to about 199 mg/dL (about 1.8 to about 2.2 mmol/L). High triglyceride levels may be about 200 to about 499 mg/dL (about 2.3 to about 5.6 mmol/L). Very high triglyceride levels may be greater than about 500 mg/dL (5.7 mmol/L).

Cholesterol may refer to another type of lipid found in blood. It may be a fat-like substance in cells. Cholesterol can contribute to plaque and atherosclerosis, which can lead to coronary artery disease. There may be several types of lipoproteins related to cholesterol: high-density lipoprotein (HDL), low-density lipoprotein (LDL), and very low-density lipoprotein (VLDL). HDL may carry cholesterol to the liver which then removes the cholesterol from the body. LDL may contribute to plaque buildup in the arteries by carrying cholesterol. VLDL may also contribute to plaque buildup in the arteries by carrying triglycerides.

A normal total cholesterol level may be less than about 200 mg/dL. Near high total cholesterol levels may be between about 200 and about 240 mg/dL. High total cholesterol levels may be greater than about 240 mg/dL.

A normal LDL cholesterol level may be less than about 100 mg/dL. Near high LDL cholesterol levels may be between about 130 and about 160 mg/dL. High LDL cholesterol levels may be between about 160 and about 190 mg/dL. Very high LDL cholesterol levels may be greater than about 190 mg/dL.

Normal HDL cholesterol levels may be above about 60 mg/dL. Dangerous HDL cholesterol levels may be less than about 40 mg/dL.

Normal VLDL cholesterol levels may be less than about 30 mg/dL. Higher VLDL cholesterol level may be greater than about 30 mg/dL. It should be appreciated that these are average values and user-specific values may vary.

Beta-cell function may refer to beta cells producing and secreting insulin, Amylin, and/or C-peptide. For example, when blood glucose levels rise, beta cells may respond by secreting insulin while increasing production of insulin. Depending on the type of diabetes, type 1 diabetes or type 2 diabetes, the beta cells may be attacked and destroyed by the immune system or are unable to produce enough insulin needed for blood sugar control, respectively.

Insulin resistance may refer to cells failing to respond to insulin properly. For example, the pancreas may overproduce insulin to lower the blood sugar leading to high insulin levels. Over time, this may increase insulin and blood sugar levels, eventually damaging the pancreas and reducing insulin production. A number of factors may indicate an insulin resistance, such as blood sugar levels, triglyceride levels, LDL levels, and HDL levels.

In another embodiment, a concentration may be monitored using an automatic reader. For example, an optical reader on a smartphone may be used to capture the lysine level, triglyceride level, cholesterol level, beta-cell function, insulin resistance, blood glucose level, HbA1c level, albumin level, creatinine level, and/or another level taken on a test. An optical reader may include a camera on a smartphone. The measurement may be captured by the optical reader using the test where the lysine level, triglyceride level, cholesterol level, beta-cell function, insulin resistance, blood glucose level, HbA1c level, albumin level, creatinine level, and/or another level was measured. In some embodiments, the value may be manually input into the automatic reader. An optical reader may capture the measurement and transmit the measurement to a data store. In some embodiments, the data store may be a remote network-based system. In some embodiments, the information on the data store may be read remotely by a caregiver or another individual. Depending on this value, the automatic reader may provide notifications on whether supplements are appropriate to administer. The notification may include a pop-up, a vibration, or a noise. The notifications may continue over time. The period between notifications may increase over time. The notifications may be stopped by user input. As more data is stored, a more precise dosage of supplements may be determined to be taken over a period of time.

In another embodiment, the test strips may be used to measure lysine levels, triglyceride levels, cholesterol levels, beta-cell function, insulin resistance levels, blood glucose levels, HbA1c levels, albumin levels, creatinine levels, the GFR, and the stage of CKD. The reader may be able to scan for these measurements. The reader may visually display these measurements to an individual. These measurements may also be sent to a remote, secure network-based data store. The measurements may be remotely accessible afterwards. In some embodiments, a user may take a test at home and the results may be immediately displayed to a remote caregiver.

Figure 11:
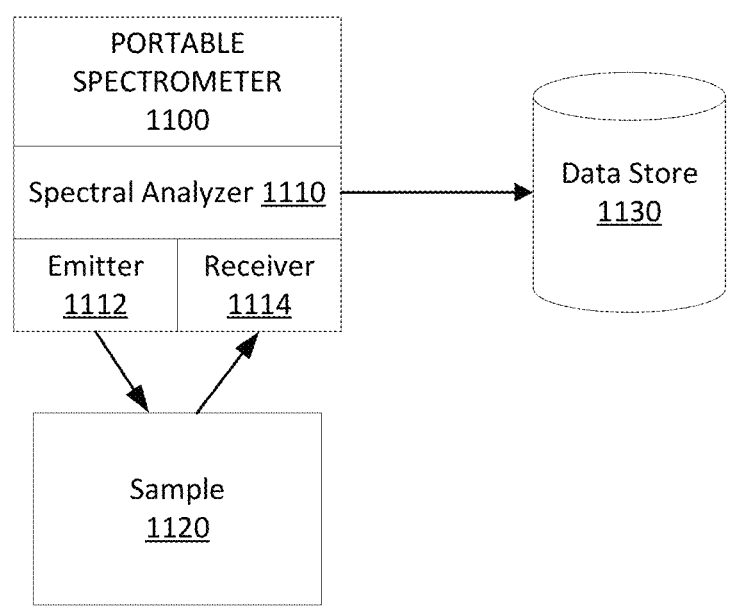
FIG. 11 is an example portable spectrometer, consistent with embodiments disclosed herein.

In some embodiments, a portable IR device, such as that shown in FIG. 11, may be used to monitor a lysine level, triglyceride level, cholesterol level, beta-cell function, insulin resistance, blood glucose level, HbA1c albumin level, creatinine level, and/or another level. The IR device may be a portable spectrometer 1100 that may be handheld. The IR device may include an emitter 1112 configured to emit electromagnetic radiation and a receiver 1114 configured to receive electromagnetic radiation reflected from a sample. Emitter 1112 may be a laser or other coherent light source, a light emitting diode, or other light source as known in the art. In some embodiments, emitter 1112 emits electromagnetic radiation in infrared wavelengths, e.g., mid-infrared (mid-IR) wavelengths between 2 micrometers and 25 micrometers. In some embodiments, emitter 1112 may include an array of multiple individual micro-emitters and a micro electro mechanical systems (MEMS) array to, for example, control shutters or filters corresponding to each micro-emitter as to control the wavelength of light transmitted from the emitter. In some embodiments, receiver 1114 may be configured to detect electromagnetic radiation in mid-IR wavelengths as well. Receiver 1114 may include an array of individual sensors, each sensitive to, or incorporated with, a spectral filter to detect and measure specific wavelengths.

In some examples, a multi-pixel sensor array may be incorporated with MEMS devices to filter out non-desired wavelengths for that pixel, and/or tune for, or enhance, the signal reception for a desired wavelength. In some examples, the MEMS sensor array may be time-sequenced to match the MEMS emitters to detect light reflected back from the sample from an individual wavelength emitted from one of the MEMS emitters. Sensors may be tuned to detect different wavelengths, such that a reflected signal from a sample may be separated into multiple wavelength components by receiver 1114, and each wavelength component may be individually measured and analyzed. Other spectral filters and/or analyzers may be used, as known in the art. In some examples, the emitter 1112 and/or receiver 1114 may be configured to operate with an electromagnetic wavelength range of between 2 micrometers and 25 micrometers.

In some embodiments, portable spectrometer 1100 may include an enclosure that is smaller than 20 cm in a first dimension, 15 cm in a second dimension, and 10 cm in height as to fit comfortably in a user's hand. Some example spectrometers may operate using an input of less than 20 volts drawing less than 5 amps. Receiver 1114 may be a pyroelectric array, CMOS chip, CCD, or other light sensor as known in the art. For example, as described above, receiver 1114 may include a spectral analyzer, such as a MEMS array, to individually tune each pixel of the light sensor to be sensitive to a desired wavelength. In some examples, the sensor may include a 256 pixel array. Other array sizes are possible. For example, adding more pixels (512, 1024, etc.) will increase the spectral resolution of the receiver. The sensor may be an ATR type sensor, for example, including Zinc Selenide.

In some embodiments, portable spectrometer 1100 may include a spectral analyzer logical circuit 1110. For example, the spectral analyzer logical circuit 1110 may include a processor and non-transitory medium with computer executable instructions embedded thereon, the computer executable instructions configured to obtain a reflection signal corresponding to a bio-sample from receiver 1114, generate a spectral profile of the bio-sample by converting a reflection signal received by receiver 1114 into an absorption spectrum. The spectrum may be generated using the MEMS filtering and/or spectral analyzer incorporated in receiver 1114. In other embodiments, a broad-band light sensor may be used and the signal may be converted into a spectrum using spectral analysis techniques as known in the art. In some embodiments, a Fourier transformation algorithm may be applied to the broad-band signal to convert the signal to a spectrum.

The computer executable instructions may also be configured to obtain a set of historical spectral profiles from data store 1130 and compare the spectral profile of the bio-sample to one or more of the historical spectral profiles. For example, the historical spectral profiles may be infra-red absorption spectral profiles for different substances that may be present in a bio-sample. In some embodiments, the substances may include triglycerides, creatinine, albumin, urea, glucose, glucosamine, fructose, fructosamine, cholesterol, hemoglobin, lysine, cholesterol, HbA1c, and/or other proteins or analytes that may absorb infrared electromagnetic radiation and reflect a detectable absorption spectrum. In some examples, the substances may also include narcotics such as opium, oxycontin, or other therapeutic or non-therapeutic drugs. The spectral profile may also be used to detect a level of one or more of these substances present in the bio-sample by comparing the relative amplitudes of the spectral signatures.

The spectral analyzer logical circuit 1110 may be communicatively coupled to the data store 130 via cellular, Wi-Fi, BLUETOOTH, or other wireless connectivity mechanisms as known in the art.

Figure 12:
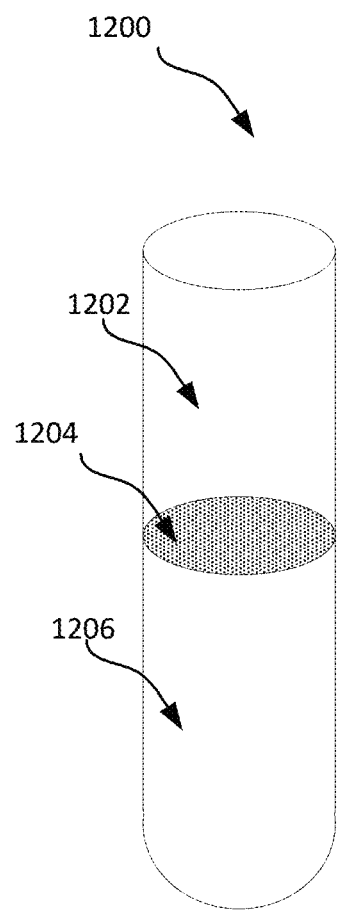
FIG. 12 illustrates an example sample fixture, consistent with embodiments disclosed herein.

The system may also include a sample fixture 1120. Sample fixture 1120 may include an attenuated total reflectance (ATR) crystal, polysulfone membrane, glass fiber membrane, paper, fiber, cloth, fabric, wood, plastic, glass, ceramic, composite, or metal substrate configured to hold, absorb, or retain a bio-sample. For example, sample fixture 1120 may be an ATR crystal, a test strip, flow cell, or other surface or enclosure configured to secure a bio-sample. FIG. 12 illustrates an example sample fixture 1200. Sample fixture 1200 may include first portion 1202 and second portion 1206 separated by porous membrane 1204. A bio-sample (not shown) may be placed into first portion 1202. Porous membrane 1204 may be shaped to filter out particles over a threshold size. For example, the threshold size may range from about 1 nanometer to about 20 micrometers. It should be appreciated that the threshold size may include other ranges of values. Porous membrane 1204 is placed near the middle of sample fixture 1200, but as will be understood by one of ordinary skill in the art, porous membrane 1204 may be located at different points in sample fixture 1200.

For example, the ATR crystal works through total internal reflection. A beam of radiation, such as mid-IR energy, passes through a crystal and undergoes total internal reflection. Evanescent waves are created that pass beyond the edges of the crystal and interact with the bio-sample. When the bio-sample absorbs the evanescent waves, absorption spectrums can be generated from the evanescent waves that are attenuated and directed to receiver 1114. The ATR crystal may be made of diamond, germanium, KRS-5, Zinc Selenide, silicon, AMTIR, and/or other materials. The ATR crystal may be set-up as a horizontal-ATR, a universal ATR, diffuse reflectance (DRIFTS), and/or other set-ups.

The bio-sample may be blood, plasma, serum, urine, or liquid suspension of cellular or tissue material extracted from a subject. The subject may be a human or animal. Sample fixture 1120 may also include an integrated needle or pointing device for breaking or piercing the subject's epidermis and capillaries to elicit the flow of blood onto the sample fixture. The bio-sample may be placed in a predetermined location on the sample fixture 1120, and the sample fixture 1120 may then be placed within optical range of the emitter 1112. In some examples, the optical range is less than about 1 m. Emitter 1112 may then be activated such that emitter 1112 emits electromagnetic radiation in the direction of sample fixture 1120, and specifically the bio-sample located on sample fixture 1120.

Sample fixture 1120 may include a membrane to help separate red blood cells used as a bio-sample. The membrane may be shaped to filter particles over a threshold size. The membrane may include polysulfone (PSF), glass fiber, and/or other materials. The membrane may help separate blood into component parts, such as blood plasma, a buffy coat, and erythrocytes. The membrane may help separate red blood cells from platelets. The membrane may help separate red blood cells from white blood cells. The membrane may separate blood cells from plasma, wherein the pore size may be about 1 micrometer. For example, PSF may be a thermoplastic material that is used to separate red blood cells. PSF may have pore sizes as small as about 10 nanometers. Sample fixture 1120 may use PSF membranes with different pore sizes to separate out blood cells into two or more groups. In another example, glass fibers may have pore sizes as small as about 1 micrometer. Similarly, sample fixture 1120 may use glass fiber membranes with different pore sizes to separate out blood cells into two or more groups.

The electromagnetic radiation may then interact with the bio-sample, and substances incorporated therein, such that particular wavelengths of electromagnetic radiation are absorbed, and other wavelengths are reflected back towards receiver 1114. In some examples, emitter 1112 may be activated using a switch located on the enclosure of the portable spectrometer 1100. In other examples, emitter 1112 may be activated through a wireless and/or wired interface using a graphical user interface (GUI), for example, from a mobile device app. Spectral data received by receiver 1114 may also be stored internally on the portable spectrometer, for example, in spectral analyzer logical circuit 1110, or transmitted via wireless or wired connectivity to data store 1130, and/or a mobile device, laptop computer, desktop computer, or cloud-based device.

Returning to FIG. 3, method 300 may also include determining any change in the dosage of the supplement including lysine, zinc, and/or vitamin C, if necessary, as in step 330. In one embodiment, a visual test, as described above, may help determine whether more or less supplements may need to be taken. In another embodiment, a specific value on a test may indicate whether more or less supplements should be taken.

Figure 4:
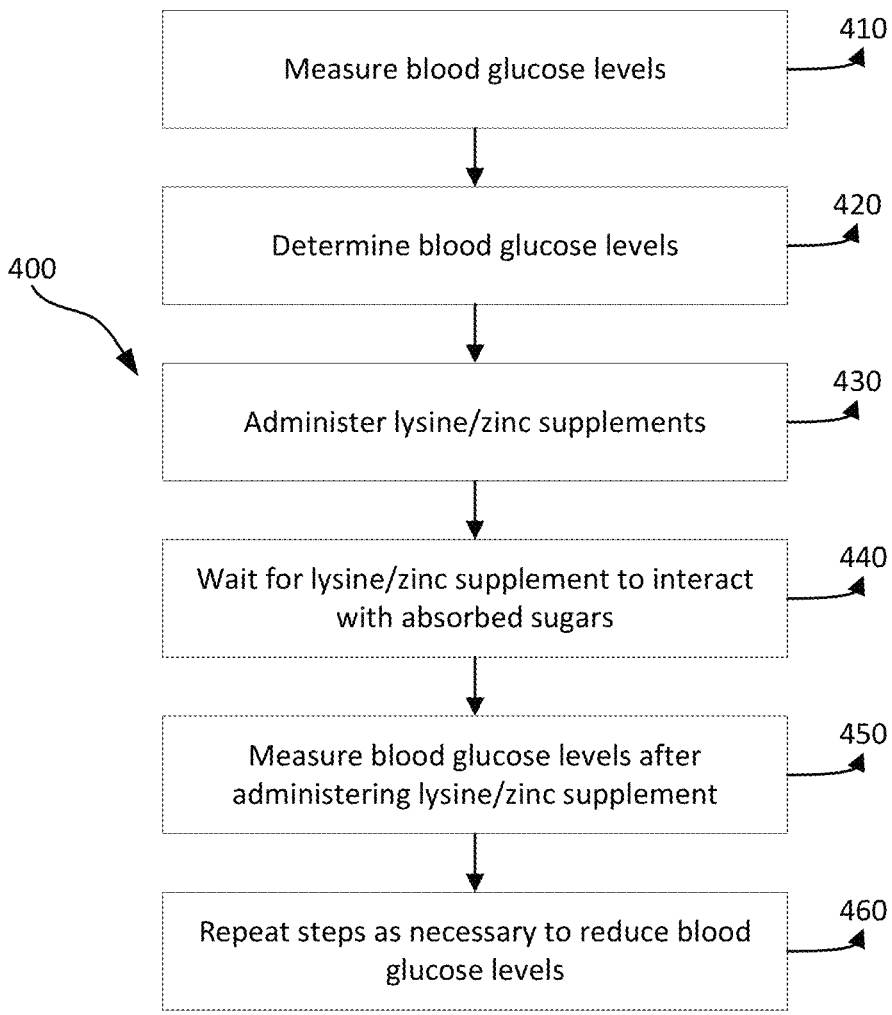
FIG. 4 is a flow chart illustrating an example method of treating diabetes using supplements including lysine, zinc, and/or vitamin C, consistent with embodiments disclosed herein.

FIG. 4 is a flow chart illustrating an example method of treating diabetes, CKD, liver disease, pancreatic ds using supplements including lysine, zinc, and/or vitamin C 400. For example, method 400 may include measuring the current blood glucose level from a test at step 410. For example, the supplement may include a range of about 500 mg to about 3000 mg of lysine, a range of about 5 mg to about 200 mg of zinc, and a range of about 50 mg to about 500 mg of vitamin C. In other embodiments, the ranges of lysine, zinc, or vitamin C may be different. In still other embodiments, the supplement may include lysine and zinc, lysine and/or vitamin C, lysine, zinc, and/or vitamin C, and/or other combinations. The test may include a fingerprick test that quantitatively indicates a blood glucose level. Method 400 may also include determining blood glucose level at step 420. Using the blood glucose level measurement from step 410, it may be determined that the blood glucose level is too high. Method 400 may also include administering supplements, based on blood glucose level at step 430. If the blood glucose level is too high, it may be appropriate to administer the supplements. The supplement may be administered in a pill, gummy form, tablet, powder for a shake, capsule, liquid extract, drink, or nutritional bar medium. The supplement may also come in various other mediums. The appropriate dosage will depend on the measured blood glucose level.

Method 400 may also include waiting for lysine to interact with absorbed sugars at step 440. After administering the supplement, a period of time should pass to allow the supplement to interact with the sugar. Method 400 may also include measuring blood glucose level after administering the supplement at step 450. After the appropriate period of time, the blood glucose level may be tested again to monitor any changes before and after the supplement was taken. If blood glucose levels are within an appropriate range, no more supplements may need to be taken. Method 400 may also include repeating the above steps as necessary to reduce blood glucose levels at step 460. If the measured blood glucose level taken after the supplement is not within an appropriate range, additional supplements may need to be taken to reduce blood glucose levels.

Figure 5:
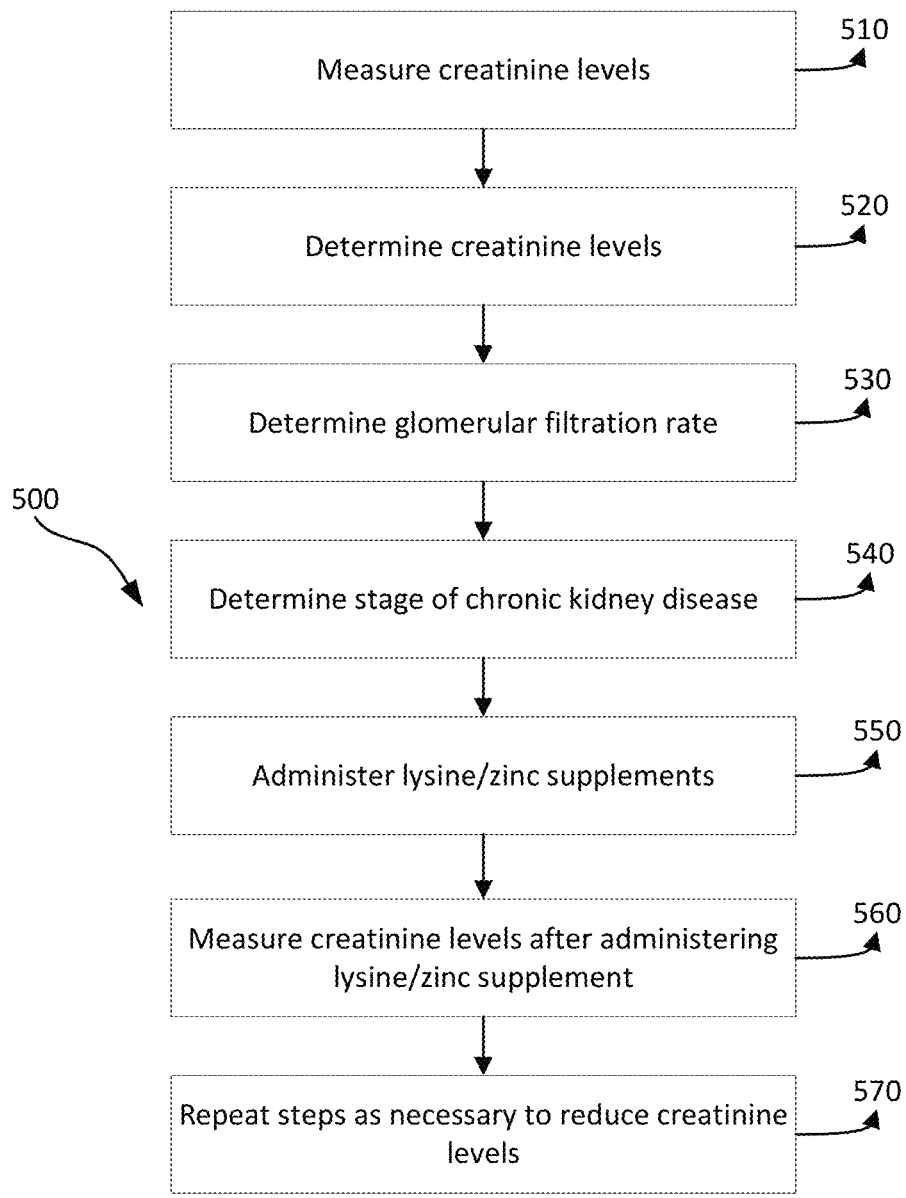
FIG. 5 is a flow chart illustrating an example method of treating chronic kidney disease using supplements including lysine, zinc, and/or vitamin C, consistent with embodiments disclosed herein.

FIG. 5 is a flow chart illustrating an example method of treating CKD using supplements including lysine, zinc, and/or vitamin C 500. For example, method 500 may include measuring the current creatinine levels from a test at step 510. Albumin levels may also be measured using a mid-IR device, as described herein. For example, the supplement may include a range of about 500 mg to about 3000 mg of lysine, a range of about 5 mg to about 200 mg of zinc, and a range of about 50 mg to about 500 mg of vitamin C. In other embodiments, the ranges of lysine, zinc, or vitamin C may be different. In still other embodiments, the supplement may include lysine and zinc, lysine and/or vitamin C, lysine, zinc, and/or vitamin C, and/or other combinations. The test may include a fingerprick test that quantitatively indicates a creatinine level and/or an albumin level. The test may include a urine test that quantitatively indicates a creatinine level and/or an albumin level. Method 500 may also include determining creatinine levels at step 520. Step 520 may also include determining albumin levels.

In another embodiment, the test may include a biochemistry test that quantitatively indicates the creatinine levels, the GFR, and the stage of CKD. A reader may be able to scan for these measurements. The reader may visually display these measurements to an individual. These measurements may also be sent to a remote, secure network-based data store. The measurements may be remotely accessible afterwards. In some embodiments, a user may take a test at home and the results may be immediately displayed to a remote caregiver.

Method 500 may also include determining a glomerular filtration rate (GFR) and/or ACR at step 530. Using the creatinine concentration measurement from step 510, an individual's weight, age, height, and other factors, the GFR may be determined. Using the creatinine concentrations and the albumin concentrations from step 510, the ACR may be determined. Method 500 may also include determining a stage of CKD at step 540. Using the GFR and/or ACR, the stage of CKD may be determined. A GFR greater than about 90 milliliters per minute per 1.73 square meters might indicate stage 1 CKD. A GFR between about 60 and about 90 milliliters per minute per 1.73 square meters might indicate stage 2 CKD. A GFR between about 30 and about 60 milliliters per minute per 1.73 square meters might indicate stage 3 CKD. A GFR between about 15 and about 30 milliliters per minute per 1.73 square meters might indicate stage 4 CKD. A GFR less than about 15 milliliters per minute per 1.73 square meters might indicate stage 5 CKD. FIG. 8 more clearly illustrates this relationship between GFR and the stage of CKD.

An ACR under 30 milligrams per gram may indicate category A1. Category A1 may indicate the ACR is normal or mildly increased. An ACR between about thirty and about 300 may indicate category A2. Category A2 may indicate the ACR is moderately increase, relative to young adult levels. For example, an ACR within the A2 category indicates CKD. An ACR over 300 milligrams per gram may indicate category A3. Category A3 may indicate ACR is severely increased. Category A3 may include nephrotic syndrome. FIG. 9 more clearly illustrates the relationship between ACR and categories in CKD.

Method 500 may also include administering supplements including lysine, zinc, and/or vitamin C, based on GFR and/or ACR at step 550. If the creatinine level and/or albumin level is too high, it may be appropriate to administer supplements including lysine, zinc, and/or vitamin C. The supplement may be administered in a pill, gummy form, tablet, powder for a shake, capsule, liquid extract, drink, or nutritional bar medium. The supplements including lysine, zinc, and/or vitamin C may also come in various other mediums. The appropriate dosage will depend on the measured creatinine level and/or albumin level.

Method 500 may also include measuring a creatinine level and/or albumin level after administering supplements including lysine, zinc, and/or vitamin C at step 560. After the appropriate period of time, the creatinine level and/or albumin level may be tested again to monitor any changes before and after the supplement was taken. If creatinine levels and/or albumin are within an appropriate range, no more supplements may need to be taken. Method 500 may also include repeating the above steps as necessary to reduce creatinine levels and/or albumin levels at step 570. If the measured creatinine level and/or albumin level taken after the supplements including lysine, zinc, and/or vitamin C is not within an appropriate range, additional supplements may need to be taken to reduce blood glucose levels.

Figure 6:
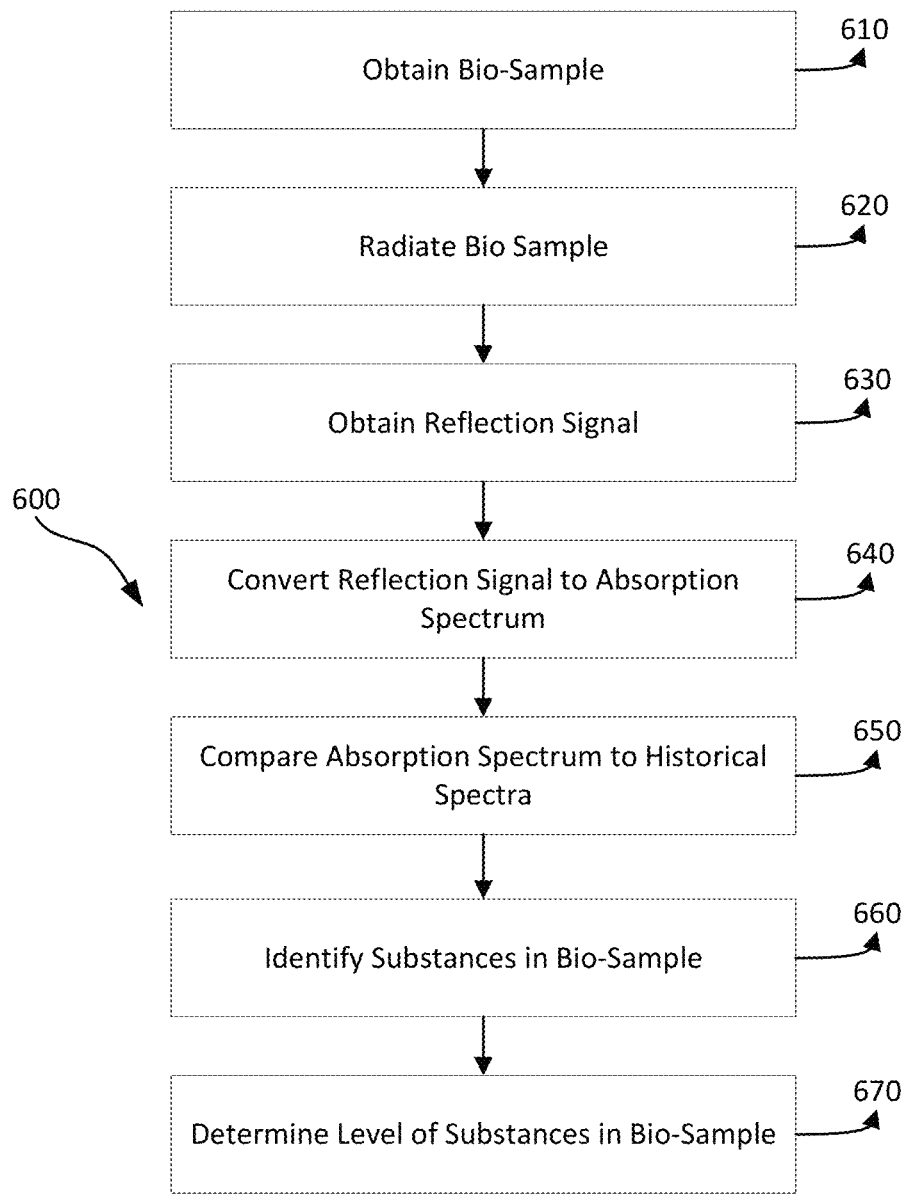
FIG. 6 is a flow chart illustrating an example method of determining levels of substances in bio-samples using a portable mid-infrared device, consistent with embodiments disclosed herein.

FIG. 6 is a flow chart illustrating an example method of determining substance levels in a bio sample using a portable IR device 600. For example, method 600 may include obtaining a bio-sample on a sample fixture at step 610. The bio-sample may be blood or urine. The sample fixture may be where the bio-sample is placed, as described above with respect to FIG. 9.

Method 600 may include radiating the bio sample with electromagnetic energy in a mid-infrared wavelength at step 620. The electromagnetic energy may come from the portable spectrometer via an emitter, as shown in FIG. 9. The mid-infrared wavelength may be a range of about 2 micrometers to about 25 micrometers. Method 600 may also include obtaining a reflection signal from the bio-sample at step 630. The portable spectrometer, as shown in FIG. 9, may be used to obtain the reflection signal via a receiver.

Method 600 may include converting the reflection signal to an absorption spectrum at step 640. The portable spectrometer, as shown in FIG. 9, may be used in converting the reflection signal. In addition, method 600 may include comparing the absorption spectrum to one or more historical absorption spectra corresponding to known substances at step 650. The known substances may include albumin and/or creatinine. Method 600 may include identifying one or more substances present in the bio-sample if the absorption spectrum substantially matches the one or more historical absorption spectra at step 660. The identified substance may be albumin and/or creatinine.

Method 600 may also include determining a level of the one or more substances present in the bio-sample based on relative amplitudes of the absorption spectrum at step 670. An albumin level and creatinine level may be determined. As a result, an ACR level may be determined.

Figure 7:
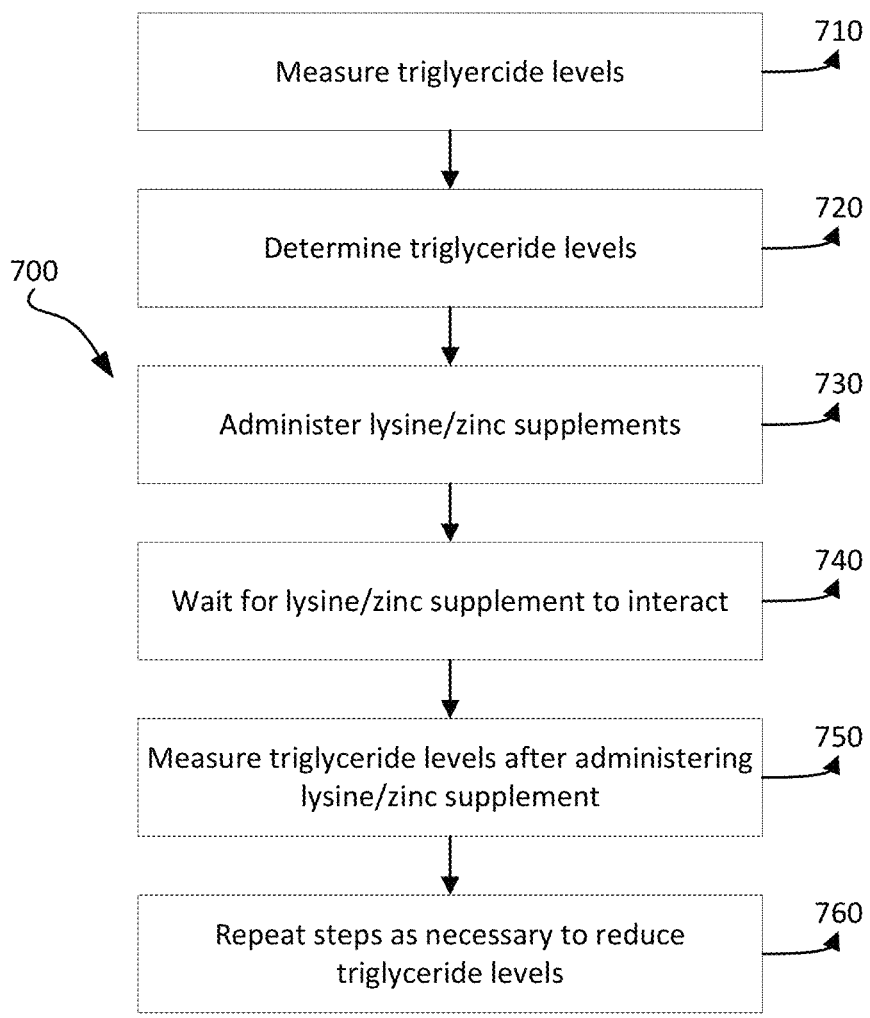
FIG. 7 is a flow chart illustrating an example method of inhibiting the effect of hepatological and pancreatic diseases using supplements including lysine, zinc, and/or vitamin C, consistent with embodiments disclosed herein.

FIG. 7 is a flow chart illustrating an example method of inhibiting the effect of hepatological and pancreatic diseases using supplements including lysine, zinc, and/or vitamin C, consistent with embodiments disclosed herein. For example, method 700 may include measuring a current triglyceride level from a test at step 710. For example, the supplement may include a range of about 500 mg to about 3000 mg of lysine, a range of about 5 mg to about 200 mg of zinc, and a range of about 50 mg to about 500 mg of vitamin C. In other embodiments, the ranges of lysine, zinc, or vitamin C may be different. In still other embodiments, the supplement may include lysine and zinc, lysine and/or vitamin C, lysine, zinc, and/or vitamin C, and/or other combinations. The test may include a fingerprick test that quantitatively indicates a triglyceride level. Triglyceride levels may also be measured using a mid-IR device, as described above in FIG. 6. The test may include a urine test that quantitatively indicates a triglyceride level.

Method 700 may also include determining the current triglyceride level at step 720. Using the triglyceride level measurement from step 710, it may be determined that the triglyceride level is too high. Method 700 may also include administering supplements, based on the triglyceride level at step 730. If the triglyceride level is too high, it may be appropriate to administer the supplements. The supplement may be administered in a pill, gummy form, tablet, powder for a shake, capsule, liquid extract, drink, or nutritional bar medium. The supplement may also come in various other mediums. The appropriate dosage will depend on the measured triglyceride level. For some patients, a triglyceride level below about 150 mg/dL may be healthy. A triglyceride level between about 150 and about 199 mg/dL may be approaching high levels of triglycerides. Patients with high triglyceride levels may have triglyceride levels between about 200 and about 299 mg/dL. Very high triglyceride levels may be above about 500 mg/dL. It should be appreciated that these values may vary based on a given user. FIG. 10 more clearly illustrates the categories of triglyceride levels.

Method 700 may also include waiting for lysine to interact with absorbed sugars at step 740. After administering the supplement, a period of time should pass to allow the supplement to interact with the sugar. Method 700 may also include measuring a triglyceride level after administering the supplement at step 750. After the appropriate period of time, the triglyceride level may be tested again to monitor any changes before and after the supplement was taken. If the triglyceride level is within an appropriate range, no more supplements may need to be taken. Method 700 may also include repeating the above steps as necessary to reduce a triglyceride level at step 760. If the measured triglyceride level taken after the supplement is not within an appropriate range, additional supplements may need to be taken to reduce triglyceride levels.

Figure 14:
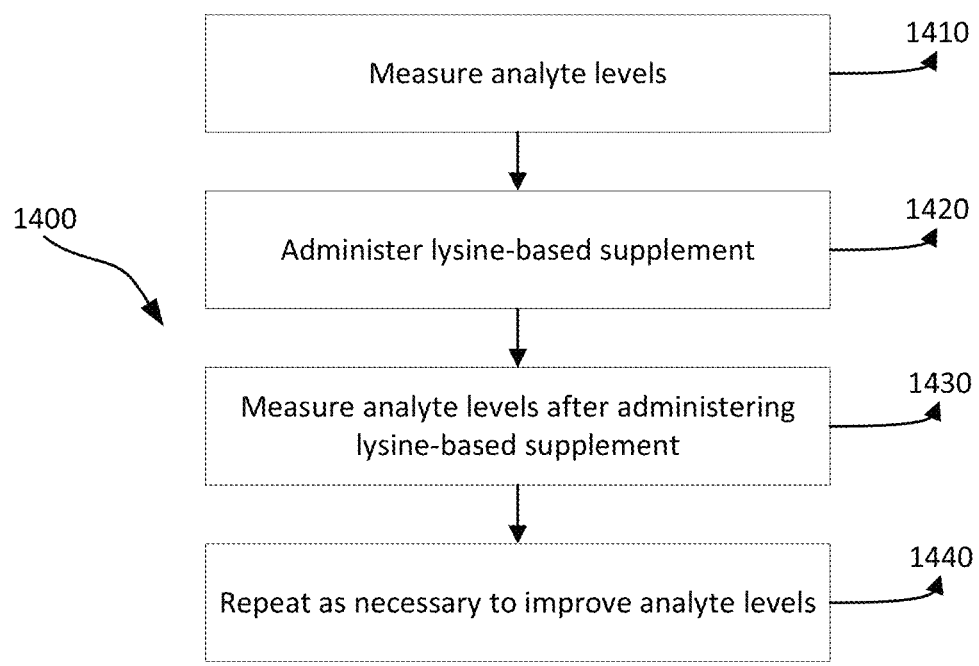
FIG. 14 is a flow chart illustrating an example method of improving lysine, triglyceride, cholesterol, beta-cell function, insulin resistance, blood glucose, and/or HbA1c levels using supplements including lysine, zinc, and/or vitamin C, in accordance with various embodiments of the present disclosure.

FIG. 14 is a flow chart illustrating an example method of improving a lysine level, triglyceride level, cholesterol level, beta-cell function, insulin resistance, blood glucose level, and/or HbA1c level using supplements including lysine, zinc, and/or vitamin C, in accordance with various embodiments of the present disclosure. For example, the supplement may include a range of about 500 mg to about 3000 mg of lysine, a range of about 5 mg to about 200 mg of zinc, and a range of about 50 mg to about 500 mg of vitamin C. In other embodiments, the ranges of lysine, zinc, or vitamin C may be different. In still other embodiments, the supplement may include lysine and zinc, lysine and vitamin C, lysine, zinc, and vitamin C, zinc and vitamin C, and/or other combinations. Method 1400 may include measuring a current value from a test at step 1410. The value may be a lysine level, triglyceride level, cholesterol level, beta-cell function, insulin resistance, blood glucose level, HbA1c level, albumin level, creatinine level, and/or another level. The test may include a fingerprick test that quantitatively indicates the value. Method 1400 may also include administering supplements at step 1420, based on the value at step 1410. Based on the value being too high, it may be appropriate to administer the supplements. The supplement may be administered in a pill, gummy form, tablet, powder for a shake, capsule, liquid extract, drink, or nutritional bar medium. The supplement may also come in various other mediums. The appropriate dosage will depend on the measured value. Method 1400 may also include step 1430, measuring a value from a test after administering the supplement at step 1420.

Method 1400 may also include waiting for lysine to interact with the body at step 1420 and 1440. After administering the supplement, a period of time should pass to allow the supplement to interact with the body. After the appropriate period of time, the analyte value may be tested again to monitor any changes before and after the supplement was taken. If the value is within an appropriate range, as discussed herein, no more supplements may need to be taken.

The data described in FIGS. 15-19 are based on a randomized, double-blind, placebo-controlled clinical trial that took place over a period of 6 months. The number of patients required for determination of a 0.5% reduction of HbA1c in the treatment group, in comparison with the placebo group at 80% power and 95% confidence interval with a drop-out rate of 20% was 108 patients. The study included more than this number: 110 subjects with pre-diabetes were randomly and equally assigned into these two groups (n=55 each), one on the supplement, and the other on a placebo. The 110 subjects were 50% (n=55) males with a mean age (±SD) of 46.7±9.9 years. The subject were randomized according to the method of block randomization with a block size of 4. The population was stratified at randomization based on age (<30 years and ≥30 years) and gender to ensure equal distribution of these variables in the two groups. Participation of the one hundred and ten patients for the 1, 3 and 6-months follow-up was 105 (supplement group—52 and placebo group—53), 94 (supplement group—49 and placebo group—45) and 83 (supplement group—45 and placebo group—38) patients respectively. Nine patients (supplement group—4 and placebo group—5) were lost to follow-up, while the remaining 18 patients discontinued the respective interventions due to development of diabetes as defined herein (supplement group—4 and placebo group—14).

The two groups were given daily supplementation. The investigators and subjects were blind to the treatment allocations. The allocation sequence number generation was done by an independent third party not involved in the trial and was kept in a secure place during the course of the study. Concealment of the randomization sequence was done by using sequentially numbered, opaque sealed envelopes. Evaluations were done at a baseline, 1, 3 and 6 months.

The inclusion criteria for the study included, a) age between 18-70 years and b) screening test confirming presence of pre-diabetes. Pre-diabetes was defined as the presence of Fasting Plasma Glucose (FPG) between about 100 to about 125 mg/dl (Impaired Fasting Glucose [IFG]) or 2-hr Post Oral Glucose Tolerance Test (OGTT) Plasma Glucose between about 140 about 199 mg/dl (Impaired Glucose Tolerance [IGT]) or both IFG and IGT or a HbA1c value between about 5.7 to about 6.4%.

The exclusion criteria for the study included, a) on any other vitamin or mineral supplementations, b) the current use of a weight loss medicine or dietary modification, c) history of diabetes mellitus, d) presently having acute diseases or other untreated illness requiring treatment, e) impaired hepatic or renal functions, f) patients with any malignancy or any other unrelated chronic illness, g) patients with cardiac, liver or respiratory failure, h) allergy to any of the constituents of the tablets, i) lactation, pregnancy or unwillingness to use an effective form of birth control for women of child bearing age and h) any condition in the opinion of the primary investigator that would affect the patient's participation.

For the study, the subject was given two tablets of the supplement as described herein, taken 1 hour before meals for a period of 6 months. The placebo tablet included inactive ingredients (magnesium stearate and microcrystalline cellulose) and was manufactured to have a similar appearance, shape, weight, taste, color, smell and texture to the supplement. This was provided 3 times a day, taken 1 hour before meals for a period of 6 months. Bottles containing a one-month supply of the tablets were given to the subjects in the respective groups at each visit. Participants in both groups received uniform advice about diet and physical activity, which are considered to be potential confounder variables affecting glycemic control.

In general, the outcome was defined as a change in glycemic control measured by HbA1c from the baseline. Other outcomes included a change in fasting plasma glucose (FPG), 2-hour OGTT plasma glucose, and a lipid profile from the baseline. Three multiple regression analyses were performed on the raw data, where change in FPG, 2-hour OGTT, and HbA1c post intervention from the baseline, respectively, were the continuous dependent variable with other independent variables.

During the 6-month follow-up period a significantly higher percentage of participants in the placebo group (25.4%,n=14) developed type 2 diabetes in comparison to the supplement group (7.3%,n=4) (p=0.018) (OR: 4.3). FPG, 2-hour OGTT, and HbA1c were significantly reduced in the supplement group only. The observed HbA1c reduction during the 6-month follow-up period in the supplement group was about 0.5%. Both total cholesterol and LDL cholesterol decreased significantly from the baseline only in the supplement group. In all three regression models the best predictor of respective dependent variable was the supplement treatment.

It should also be noted that the analysis of the food frequency questionnaires at each visit (0-3) did not reveal a significant difference in the energy, carbohydrate, protein, fat and dietary fiber intake between the two groups. Physical activity (total MET minutes/week) was also similar between groups and within groups at baseline, 3 months and 6 months. Finally, there were no serious adverse effects noted, and none of the subjects were hospitalized due to adverse effects during the 6 months follow up period. No hypoglycemic episodes were reported in the study participants. Biochemical assessments evaluating potential target organ toxicity (e.g., liver enzymes, serum bilirubin and serum creatinine) remained normal throughout the study period. None of the patients experienced any form of hypersensitivity during the study (immediate and/or delayed). Drug compliance (%) of patients was evaluated by pill counting. The mean % compliance (±SD) during the 1st month, 3rd month and 6th month in the supplement group was 90.8±19.2, 91.2±10.6, 92.5±10.1 and 90.6±19.1 respectively. A similar compliance was noted in the placebo group (91.9±19.7, 90.1±10.6, 91.7±11.5 and 93.5±6.1 respectively). There was no significant difference between the mean % compliances of the two groups.

FIG. 15 illustrates the effect of the supplement on a sample group compared to a group on placebos, in accordance with various embodiments of the present disclosure. FIG. 15 is based on the study described herein and illustrates the baseline characteristics of the two groups. The only values with any significant differences are the total cholesterol and daily fat intake, which only make about a 6% difference and about a 12% difference, respectively, from the greater number.

FIG. 16 illustrates the effect of the supplement on a sample group compared to a group on placebos, in accordance with various embodiments of the present disclosure. FIG. 16 is based on the study described herein and illustrates the change in glycemic control, insulin resistance, and beta-cell function in the two groups over 6 months. As illustrated, during the 6-month follow-up period a significantly higher percentage of participants in the placebo group (25.4%, n=14) developed type 2 diabetes in comparison to the supplement group (7.3%, n=4) (p=0.018) (OR: 4.3 [95% CI 1.3-14.2]). The FPG significantly reduced in the supplement group at 3 months, and this reduction was sustained during the 6-month follow-up period. However, this was not observed in the placebo group. A similar reduction was observed in the 2-hour OGTT plasma glucose values and HbA1c only in the supplement group, whereas in the placebo group they either remained unchanged or significantly increased. Finally, the observed HbA1c reduction during the 6-month follow-up period in the supplement group is about 0.5%. Insulin resistance (HOMA-IR) decreased significantly from baseline to 6 months in the supplement group, with significant improvement in β-cell function (HOMA-β), while this was not observed in the placebo group.

FIG. 17 illustrates the effect of the supplement on a sample group compared to a group on placebos, in accordance with various embodiments of the present disclosure. FIG. 17 is based on the study described herein and illustrates the change in cholesterol and triglycerides in the two groups over 6 months. As illustrated, total cholesterol and LDL cholesterol decreased significantly from baseline in the supplement group and remained unchanged in the placebo group.

FIG. 18 illustrates the effect of the supplement on a sample group compared to a group on placebos, in accordance with various embodiments of the present disclosure. FIG. 17 is based on the study described herein and illustrates the three regression models. They were statistically significant with an adjusted $R^2$ of 0.432 (FPG), 0.511 (OGTT) and 0.329 (HbA1c). Significant predictors of change in FPG from baseline were, age, carbohydrate intake and supplement treatment. Change in 2-hour OGTT plasma glucose was predicted by carbohydrate intake, baseline 2-hour OGTT value and supplement treatment. Similar results were observed for HbA1c, where carbohydrate intake and supplement treatment were the significant predictors of HbA1c. In all three regression models, the best predictor of the respective dependent variable was supplement treatment.

As used herein, the terms logical circuit and engine might describe a given unit of functionality that may be performed in accordance with one or more embodiments of the technology disclosed herein. As used herein, either a logical circuit or an engine might be implemented utilizing any form of hardware, software, or a combination thereof. For example, one or more processors, controllers, ASICs, PLAs, PALs, CPLDs, FPGAs, logical components, software routines or other mechanisms might be implemented to make up an engine. In implementation, the various engines described herein might be implemented as discrete engines or the functions and features described may be shared in part or in total among one or more engines. In other words, as would be apparent to one of ordinary skill in the art after reading this description, the various features and functionality described herein may be implemented in any given application and may be implemented in one or more separate or shared engines in various combinations and permutations. Even though various features or elements of functionality may be individually described or claimed as separate engines, one of ordinary skill in the art will understand that these features and functionality may be shared among one or more common software and hardware elements, and such description shall not require or imply that separate hardware or software components are used to implement such features or functionality.

Where components, logical circuits, or engines of the technology are implemented in whole or in part using software, in one embodiment, these software elements may be implemented to operate with a computing or logical circuit capable of carrying out the functionality described with respect thereto. After reading this description, it will become apparent to a person skilled in the relevant art how to implement the technology using other logical circuits or architectures.

Figure 13:
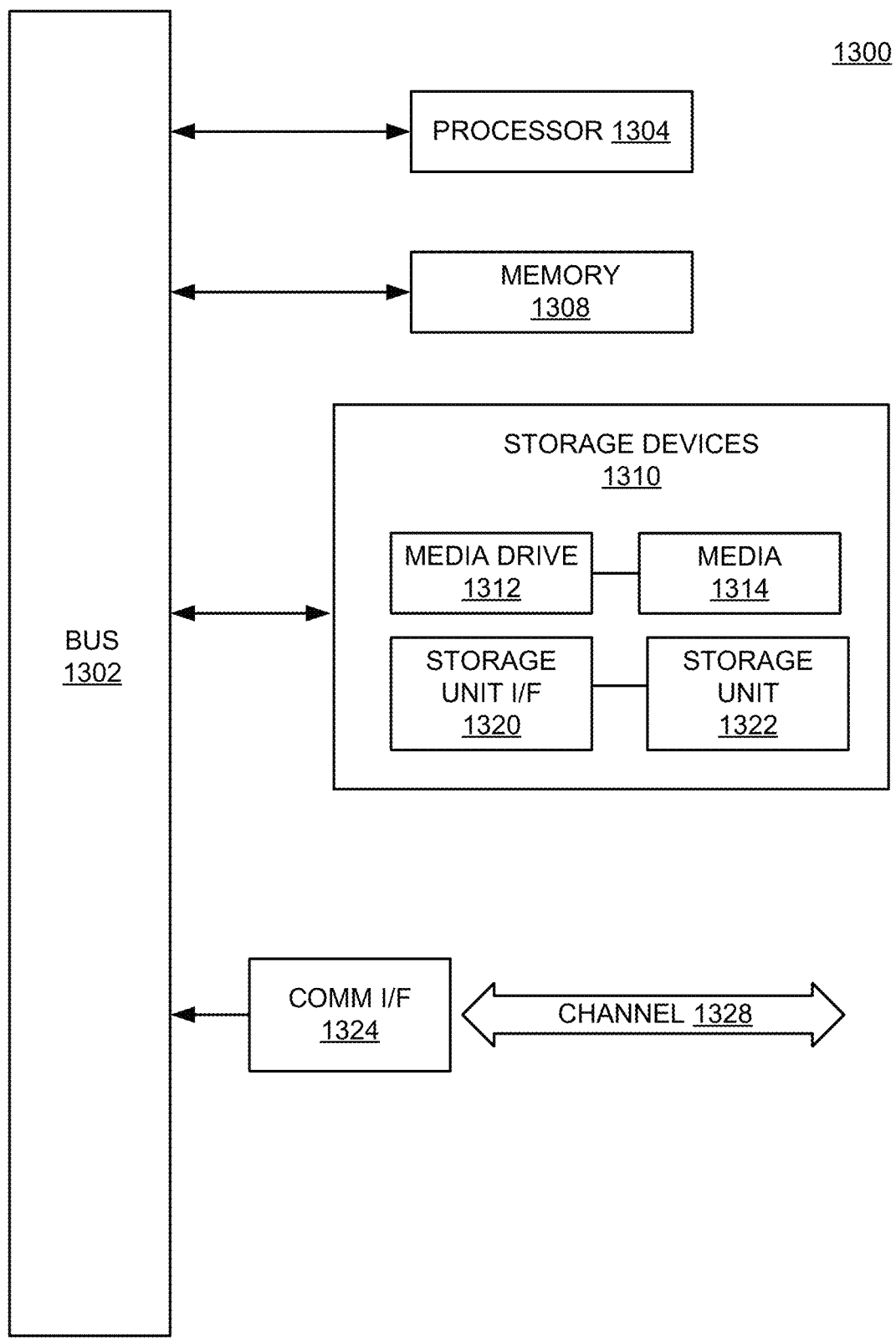
FIG. 13 is a diagram illustrating an exemplary computing module that may be used to implement any of the embodiments disclosed herein.

Referring now to FIG. 13, computing system 1300 may represent, for example, computing or processing capabilities found within desktop, laptop and notebook computers; hand-held computing devices (PDA's, smart phones, cell phones, palmtops, etc.); mainframes, supercomputers, workstations or servers; or any other type of special-purpose or general-purpose computing devices as may be desirable or appropriate for a given application or environment. Logical circuit 1300 might also represent computing capabilities embedded within or otherwise available to a given device. For example, a logical circuit might be found in other electronic devices such as, for example, digital cameras, navigation systems, cellular telephones, portable computing devices, modems, routers, WAPs, terminals and other electronic devices that might include some form of processing capability.

Computing system 1300 might include, for example, one or more processors, controllers, control engines, or other processing devices, such as a processor 1304. Processor 1304 might be implemented using a general-purpose or special-purpose processing engine such as, for example, a microprocessor, controller, or other control logic. In the illustrated example, processor 1304 is connected to a bus 1302, although any communication medium may be used to facilitate interaction with other components of logical circuit 1300 or to communicate externally.

Computing system 1300 might also include one or more memory engines, simply referred to herein as main memory 1308. For example, preferably random access memory (RAM) or other dynamic memory, might be used for storing information and instructions to be executed by processor 1304. Main memory 1308 might also be used for storing temporary variables or other intermediate information during execution of instructions to be executed by processor 1304. Logical circuit 1300 might likewise include a read only memory ("ROM") or other static storage device coupled to bus 1302 for storing static information and instructions for processor 1304.

The computing system 1300 might also include one or more various forms of information storage mechanism 1310, which might include, for example, a media drive 1312 and a storage unit interface 1320. The media drive 1312 might include a drive or other mechanism to support fixed or removable storage media 1314. For example, a hard disk drive, a floppy disk drive, a magnetic tape drive, an optical disk drive, a CD or DVD drive (R or RW), or other removable or fixed media drive might be provided. Accordingly, storage media 1314 might include, for example, a hard disk, a floppy disk, magnetic tape, cartridge, optical disk, a CD or DVD, or other fixed or removable medium that is read by, written to or accessed by media drive 1312. As these examples illustrate, the storage media 1314 can include a computer usable storage medium having stored therein computer software or data.

In alternative embodiments, information storage mechanism 1310 might include other similar instrumentalities for allowing computer programs or other instructions or data to be loaded into logical circuit 1300. Such instrumentalities might include, for example, a fixed or removable storage unit 1322 and an interface 1320. Examples of such storage units 1322 and interfaces 1320 can include a program cartridge and cartridge interface, a removable memory (for example, a flash memory or other removable memory engine) and memory slot, a PCMCIA slot and card, and other fixed or removable storage units 1322 and interfaces 1320 that allow software and data to be transferred from the storage unit 1322 to logical circuit 1300.

Logical circuit 1300 might also include a communications interface 1326. Communications interface 1326 might be used to allow software and data to be transferred between logical circuit 1300 and external devices. Examples of communications interface 1326 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or another communications interface. Software and data transferred via communications interface 1326 might typically be carried on signals, which can be electronic, electromagnetic (which includes optical) or other signals capable of being exchanged by a given communications interface 1326. These signals might be provided to communications interface 1326 via a channel 1328. This channel 1328 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 1308, storage unit 1320, media 1314, and channel 1328. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the logical circuit 1300 to perform features or functions of the disclosed technology as discussed herein.

Although FIG. 13 depicts a computer network, it is understood that the disclosure is not limited to operation with a computer network, but rather, the disclosure may be practiced in any suitable electronic device. Accordingly, the computer network depicted in FIG. 13 is for illustrative purposes only and thus is not meant to limit the disclosure in any respect.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent engine names other than those depicted herein can be applied to the various partitions.

Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "engine" does not imply that the components or functionality described or claimed as part of the engine are all configured in a common package. Indeed, any or all of the various components of an engine, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A method of monitoring an analyte level, the method comprising:
   administering a supplement consisting of lysine, zinc, and vitamin C to a user; and
   monitoring an analyte level in a bio-sample before and after the supplement is administered, wherein the analyte is selected from the group consisting of lysine, triglyceride, cholesterol, blood glucose, HbA1c, albumin, and creatinine.

2. The method of claim 1, wherein a lysine portion of the supplement comprises D-lysine.

3. The method of claim 1, wherein a lysine portion of the supplement comprises L-lysine.

4. The method of claim 1, wherein monitoring the analyte level comprises analyzing blood samples.

5. The method of claim 1, wherein monitoring the analyte level comprises analyzing urine samples.

6. The method of claim 1, wherein the analyte level is selected from the group consisting of a lysine level, triglyceride level, cholesterol level, beta-cell function, insulin resistance, blood glucose level, HbA1c level, albumin level, and creatinine level.

7. The method of claim 1, wherein the supplement comprises a range of about 500 mg to about 3000 mg of lysine.

8. The method of claim 1, wherein the supplement comprises a range of less than about 200 mg of zinc.

9. The method of claim 1, wherein the supplement comprises a range of about 500 mg to about 2000 mg of lysine, less than about 200 mg of zinc, and less than about 500 mg of vitamin C.

10. A method of improving an analyte level in a user, the method comprising:
    administering a supplement consisting of lysine, zinc, and vitamin C to the user;
    monitoring an analyte level in a bio-sample before and after the supplement is administered, wherein the analyte is selected from the group consisting of lysine, triglyceride, cholesterol, blood glucose, HbA1c, albumin, and creatinine; and
    determining a change in a dose of the supplement based on the analyte level found in the bio-sample after the supplement is administered.

11. The method of claim 10, further comprising providing a notification on an automatic reader regarding a precise dosage of supplement to be administered.

12. The method of claim 11, wherein the notification comprises a pop-up, a vibration, or a noise.

13. The method of claim 10, wherein determining a change in dose comprises using a visual test to determine an amount of supplement to be administered, wherein the visual test comprises exposing the bio-sample to a reagent that causes a visible indication of the analyte level within the bio-sample.

14. The method of claim 10, wherein the analyte level is selected from he group consisting of a lysine level, triglyceride level, cholesterol level, beta-cell function, insulin resistance, blood glucose level, HbA1c level, albumin level, and creatinine level.

15. The method of claim 10, wherein the supplement comprises a range of about 500 mg to about 2000 mg of lysine, less than about 200 mg of zinc, and less than about 500 mg of vitamin C.

16. A method of improving an insulin resistance for a user with pre-diabetes, the method consisting of administering a supplement comprising lysine, zinc, and vitamin C to the user with pre-diabetes.

17. A method of improving a beta-cell function for a user with pre-diabetes, the method consisting of administering a supplement comprising lysine, zinc, and vitamin C to the user with pre-diabetes.

18. A method of reducing the progression to diabetes for a user with pre-diabetes, the method consisting of administering a supplement comprising lysine, zinc, and vitamin C to the user with pre-diabetes.

* * * * *